(12) United States Patent
Armstrong et al.

(10) Patent No.: US 6,780,649 B2
(45) Date of Patent: Aug. 24, 2004

(54) PHOTOLUMINESCENT SEMICONDUCTOR MATERIALS

(75) Inventors: David W. Armstrong, Ottawa (CA); Martine L. Lafrance, Ottawa (CA)

(73) Assignee: Iatroquest Corporation, Ontario (CA)

( * ) Notice: Subject to any disclaimer, the term of this patent is extended or adjusted under 35 U.S.C. 154(b) by 107 days.

(21) Appl. No.: 10/228,203

(22) Filed: Aug. 27, 2002

(65) Prior Publication Data

US 2003/0129764 A1 Jul. 10, 2003

Related U.S. Application Data

(62) Division of application No. 09/350,513, filed on Jul. 9, 1999, now Pat. No. 6,630,356.
(60) Provisional application No. 60/092,454, filed on Jul. 10, 1998.

(51) Int. Cl.[7] .......................... G01N 21/76; G01N 33/00
(52) U.S. Cl. ...................... 436/172; 436/72; 422/82.05; 422/82.08; 422/82.09; 204/403; 257/1; 205/118; 205/122; 205/792; 205/793
(58) Field of Search ................ 436/172, 72; 422/82.05, 422/82.08, 82.09; 204/403; 257/1; 205/118, 122, 123, 792, 793

(56) References Cited

U.S. PATENT DOCUMENTS

| | | | |
|---|---|---|---|
| 5,338,415 A | 8/1994 | Sailor et al. | 204/129.2 |
| 5,397,429 A | 3/1995 | Hummel et al. | 156/643 |
| 5,453,624 A | 9/1995 | Sailor et al. | 250/458.1 |
| 5,585,646 A | 12/1996 | Kossovsky et al. | 257/40 |
| 5,670,827 A | 9/1997 | Sakuma et al. | 257/741 |
| 5,869,244 A | 2/1999 | Martin et al. | 435/6 |
| 5,874,047 A | 2/1999 | Schoning et al. | 422/82.02 |
| 5,990,479 A | 11/1999 | Weiss et al. | 250/307 |

FOREIGN PATENT DOCUMENTS

| | | | |
|---|---|---|---|
| WO | WO 98/25090 | 6/1998 | F27B/15/00 |

OTHER PUBLICATIONS

Anderson et al "Chemical Surface Modification of Porous Silicon" *J Electrochem Soc* 140:5:1393–6;1993.
Bressers et al "Etching and Electrochemistry of Silicon in Acidic Bromine Solutions" *J Electroanalytical Chemistry* 406:131–7;1996.
Canham "Silicon Quantum Wire Array Fabrication by Electrochemical and Chemical Dissolution of Wafers" *Appl Phys Lett* 57:10:1046–1048; 1990.
Cullis et al "Visible Light Emission due to Quantum Size Effects in Highly Porous Crystalline Silicon" *Nature* 353:335–338; Sep. 26, 1991.
Duvault–Herrera et al "Quantitative Study of the Hydroxylation and of the Chemical Grafting of Oxidized Porous Silicon" *Colloids Surf* 50:197–206;1990.
Fathauer et al "Visible luminescence from silicon wafers subjected to stain etches" *Appl Phys Lett* 60:8:995–997; Feb. 24, 1992.
Fauchet "Photoluminescence and Electroluminescence from Porous Silicon" *J Luminescence* 70:294–309; 1996.

(List continued on next page.)

Primary Examiner—Jill Warden
Assistant Examiner—Monique T. Cole
(74) Attorney, Agent, or Firm—Heller Ehrman White and McAuliffe LLP

(57) ABSTRACT

Semiconductor materials having a porous texture are modified with a recognition element and produce a photoluminescent response on exposure to electromagnetic radiation. The recognition elements, which can be selected from biomolecular, organic and inorganic moieties, interact with a target analyte to produce a modulated photoluminescent response, as compared with that of semiconductor materials modified with a recognition element only.

34 Claims, 7 Drawing Sheets

OTHER PUBLICATIONS

Foucaran et al "Porous Silicon Layers used for Gas Sensor Applications" *Thin Solid Films* 297:317–320; 1997.

Hirschman et al "Silicon–Based Visible Light–Emitting Devices Integrated into Microelectronic Circuits" *Nature* 384:338–341; Nov. 28, 1996.

Janshoff et al "Macroporous p–Type Silicon Fabry–Perot Layers, Fabrication, Characterization, and Applications in Biosensing" *J Am Chem Soc* 120:12108–12116; 1998 (Published no earlier than 08/98)

Kurmaev et al "X–Ray emission Spectra and the Effect of Oxidation on the Local Structure of Porous and Spark–Processed Silicon" *J Phys Condens Matter* 9:2671–2681; 1997.

Lauerhaas et al "Chemical Modification of the Photoluminescence Quenching of Porous Silicon" *Science* 261:1567–1568; Sep. 17, 1993.

Lee et al "Chemical Modification of the Porous Silicon Surface" *Mater Res Soc Symp Proc* 358:387–392; 1995.

Lee et al "Chemical Modification of the Porous Silicon Si Surfaces with Carboxylic Acids" *J Am Chem Soc* 118: 5375–5382; 1996.

Li et al "Chemically Induced Shifts in the Photoluminescence Spectra of Porous Silicon" *Appl Phys Lett* 62:24:3192–3194;1993.

Lin et al "A Porous Silicon–Based Optical Interferometric Biosensor" *Science* 278:840–843; Oct. 31, 1997.

Liu et al "Stable Blue–Green and Ultraviolet Photoluminescence from Silicon Carbide on Porous Silicon" *Solid State Communications* 106:4:211–214; 1998 (Published no earlier than Jan. 1998).

Nakajima et al "Photoluminescence of Porous Si, Oxidized then Deoxidized Chemically" *Appl Phys Lett* 61:1:46–48;1992.

Petrova–Koch et al "Rapid–Thermal–Oxidized Porous Si—The Superior Photoluminescence Si" *Appl Phys Lett* 61:8:943–945;1992.

Sailor et al "Porous Silicon—What is Responsible for the Visible Luminescence?" *Adv Mater* 4:6:432–434; 1992.

Sailor et al "Surface Chemistry of Luminescent Silicon Nanocrystallites" *Adv Mater* 9:10:783–793; 1997.

Schmuki et al "Light Emitting Micropatterns of Porous Si Created at Surface Defects" *Phys Rev Letters* 80: 18: 4060–4063; May 4, 1998.

Schmuki et al "Formation of Visible Light Emitting Porous GaAs Micropatterns" *Appl Phys Lett* 72:9:1039–1041; Mar. 2, 1998.

Shane et al "The Effects of Surfactants on the Photoluminescence of Porous Silicon" *Electrochem Soc Proc* 95–25:278–285; 1995.

Solomon et al "Spatial and quantum confinement in crystalline and amorphous porous silicon" *J Non–Cryst Solids* 227:230:Part 1:248–253; May 1998.

Song et al "Quenching of Photoluminescence from Porous Silicon by Aromatic Molecules" *J Am Chem Soc* 119: 7381–7385; 1997.

Tsai et al "Correlation Between Silicon Hydride Species and the Photoluminescence Intensity of Porous Silicon" *Appl Phys Lett* 60:14:1700–1702; Apr. 6, 1992.

Vasquez et al "Electronic structure of light–emitting porous Si" *Appl Phys Lett* 60:8:1004–1006; Feb. 24, 1992.

Yamada et al "Optical Properties of Silicon Nanocrystallites Prepared by Excimer Laser Ablation in Inerts Gas" *Japanese J Appl Physics Part 1—Regular Papers Short Note* 35:1361–1365; Feb. 1996.

Yamana et al "Porous Silicon Oxide Layer Formation by the Electrochemical Treatment of a Porous Layer" *J Electrochem Soc* 137:9:2925–2927; Sep. 1990.

PHOTOLUMINESCENT SEMICONDUCTOR MATERIALS

This application is a divisional of Ser. No. 09/350,513, filed Jul. 9, 1999 now U.S. Pat. No. 6,630,356 which claims the benefit of No. 60/092,454 filed Jul. 10, 1998.

FIELD OF THE INVENTION

The present invention relates to materials for photodetection and identification of target analytes, in particular, to materials having light-emitting properties and, more particularly, to photoluminescent semiconductor materials for photodetection and identification of target analytes.

BACKGROUND OF THE INVENTION

Porous silicon (PSi) has been extensively studied for a number of semiconductor applications since it was discovered in the late 1950's. More recently, PSi has been shown to exhibit strong visible luminescence (Canham *Appl Phys Lett* 57:1046; 1990), suggesting promising applications in silicon-based opto-electronic devices. Other porous semiconductor materials such as gallium arsenide, for example, have also been studied to a lesser extent (Schmuki et al *Appl Phys Lett* 72:1039; 1998).

U.S. Pat. Nos. 5,338,415 and 5,453,624 (Sailor et al) describe a method for detection of chemicals by reversible quenching of PSi photoluminescence and a device for detection of organic solvents by PSi photoluminescence, respectively. A silicon wafer was electrochemically etched (anodization) with a 50:50 ethanol/hydrofluoric acid (HF) solution to produce a PSi wafer. When the PSi wafer was illuminated with a laser light source in the presence of an organic compound, such as tetrahydrofuran (THF), diethyl ether, methylene chloride ($MeCl_2$), toluene, o-xylene, ethanol and methanol (MeOH), the inherent luminescent emission intensity of the PSi was significantly decreased (i.e., the photoluminescent response of the PSi was quenched). Also, Sailor observed that a toluene based solution of ferrocene (i.e., dicyclopentadienyl Fe (II)) resulted in a complete loss of luminescence.

Generally, Sailor suggests that the degree of quenching in the photoluminescent (PL) response tracks with the dipole moment of the compounds evaluated. Accordingly, these studies suggest that such an evaluation technique can help assess the differences in dipole moments between certain organic compounds. However, Sailor fails to suggest how such a method could distinguish between two or more compounds having similar dipole moments, but otherwise very different chemical compositions. For example, in U.S. Pat. No. 5,338,415, Sailor observed that $MeCl_2$, MeOH and THF all had luminescent quenching ratios of about 0.1 or less. Consequently, there is only a small difference in the PL response curves produced by each of these compounds, which could be used to better characterize their respective chemical structures. Also, Sailor discloses a reversible wavelength ("λ") shift of about 30 nanometers (nm, $10^{-9}$ m), from 670 nm to 630 nm, when PSi is exposed to THF. He suggests that the other organic compounds evaluated produce reversible quenching, but fails to suggest that the λ shift is similar to the λ shift observed for THF. However, on its face, it appears that Sailor is suggesting that the λ shifts are substantially similar in magnitude and direction for all organic compounds evaluated. Accordingly, this 30 nm range provides a somewhat limited window for spectroscopically discriminating between unknown compounds.

Lin et al describe a biosensor based on induced wavelength shifts in the Fabry-Perot fringes in the visible light reflection spectrum of a thin flat film of PSi (*Science* 278:840; Oct 31, 1997). Optically flat thin films of PSi, prepared by electrochemical etching with a 98% ethanol: 49% aqueous HF solution, are sufficiently transparent to display Fabry-Perot fringes in their optical reflection spectrum. A recognition element is immobilized on the flat PSi film. Subsequent binding of an analyte to the recognition element therefore results in a change in the refractive index of the PSi film and is detected as a corresponding shift in the interference pattern. The interference pattern is created by reflectance of white light and an interference pattern produced when multiple reflections of white light are directed toward a solution/PSi interface and a PSi/bulk silicon interface. Producing and maintaining nearly perfectly parallel planes between the air/PSi and PSi/bulk silicon interfaces is critical to producing precise and accurate interferometric spectra. Consequently, this technique is limited to applications where environmental conditions such as vibration, temperature and atmospheric gases can be precisely controlled.

Janshoff et al (*J Am Chem Soc* 120:12108–12116; 1998) also describe PSi for biosensor applications utilizing a shift in a Fabry-Perot fringe pattern, created by multiple reflections of illuminated white light on the air/PSi layer and PSi/bulk silicon interface, as a means for detecting molecular interactions of species in solution with immobilized ligands as receptors. Janshoff et al state that "the prerequisite for using porous silicon as an optical interferometric biosensor is to adjust the size as well as the geometrical shape of the pores by choosing the appropriate etching parameters" (p.12108). Thin films of silicon were made porous using electrochemical etching to produce pores having radii varying from 3 to 10 nm, a uniform depth, and cylindrical shape with an absolute surface area of about 0.1 to 0.15 $m^2$ for samples etched into a 1 $cm^2$ patch of silicon. Excessive porosity was found to be unsuitable for the biosensors of Janshoff et al.

Because interferometric techniques exploit a physical phenomenon, namely, reflectance of light by two different planes to produce an interference pattern, biosensor systems relying on shifts in the interference pattern as a means for detecting the presence of an analyte are typically very sensitive to vibration, temperature and atmospheric pressure changes. Furthermore, the reflective plates of the film or wafer, i.e. the air/PSi and the PSi/bulk silicon interfaces, must be parallel, otherwise an undesired shift in the interference pattern can occur. Typically, the reflective plates of the PSi film must be parallel to 25 Å (2.5 nm). This demands a high level of perfection in manufacture of the PSi wafer or film. Finally, for optimum performance, the irradiated light directed on the PSi film or wafer should be perpendicular to the reflective plates. Accordingly, pores which themselves are not perpendicular to the reflective plates affect the interference pattern of the PSi film or wafer and therefore adversely affect results obtained from such biosensors.

It would therefore be desirable to have a material useful for detecting target compounds, which can use the photoluminescence properties of porous semiconductor materials. Moreover, such material could be modified to provide increased sensitivity to quantitatively detecting low concentrations of predetermined target compounds.

SUMMARY OF THE INVENTION

According to one aspect of the present invention, there is provided a modified semiconductor composition comprising: (a) at least one a semiconductor material having a porous texture and (b) at least one recognition element, whereby when said composition is irradiated with at least one wavelength of electromagnetic radiation in the range of from about 100 nm to about 1000 nm, said composition produces at least one first luminescent response in the range of from about 200 nm to about 800 nm.

According to another aspect of the present invention, there is provided a method for producing a luminescent response, comprising: (a) providing a modified semiconductor composition comprising a semiconductor material having a porous texture and at least one recognition element; (b) irradiating at least said modified semiconductor composition with at least one wavelength of electromagnetic radiation in the range of from about 100 nm to about 1000 nm to produce at least one first luminescent response; and measuring at least the intensity or wavelength of said at least one first luminescent response.

BRIEF DESCRIPTION OF THE DRAWINGS

In drawings which illustrate embodiments of the present invention.

DETAILED DESCRIPTION OF PREFERRED EMBODIMENTS

Figure 1:
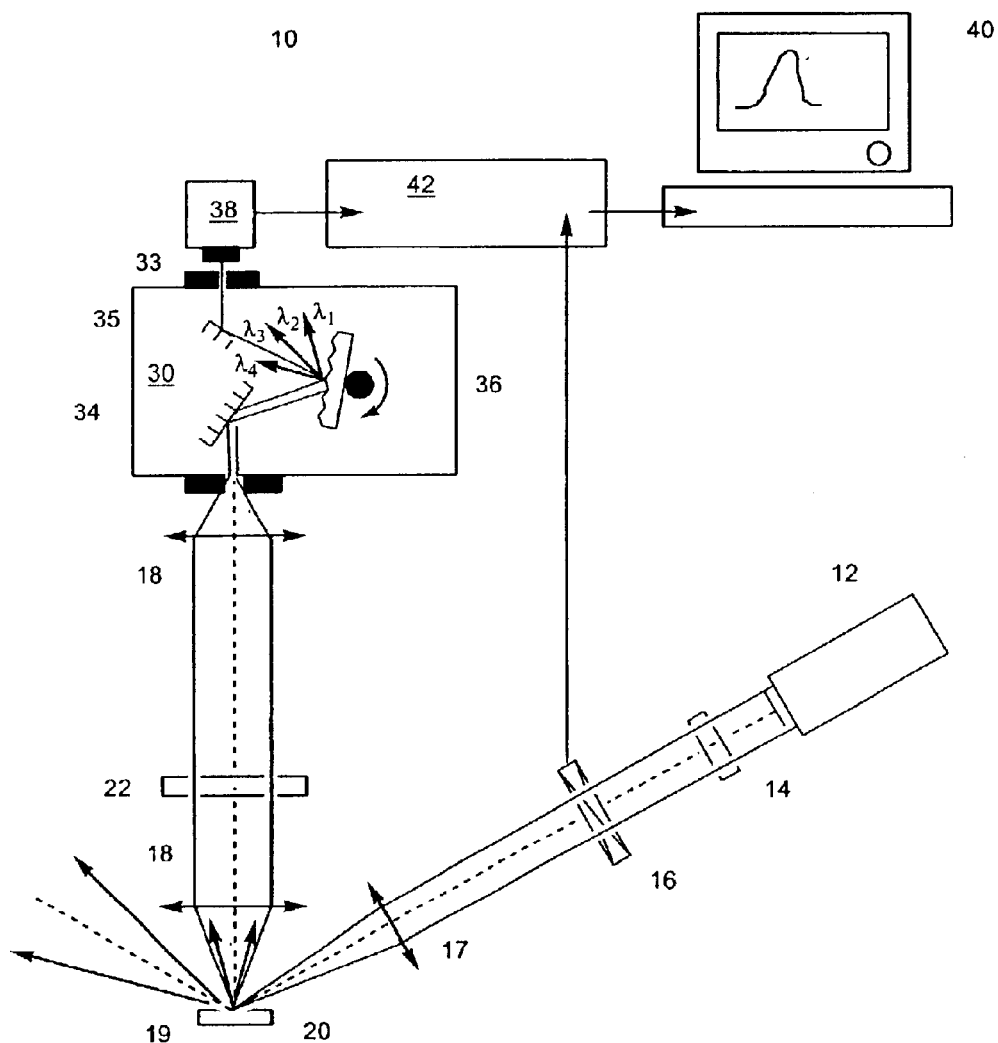
FIG. 1 is a schematic representation of one embodiment of an apparatus which can be used to detect photoluminescence from photoluminescent devices of the present invention.

As disclosed herein, the porous semiconductor (PSc) materials of the invention have photoluminescent (PL) properties and can be used in a variety of analyte detection applications, including, without limitation, biotechnology, such as biosensors for medical, environmental, industrial and defense applications (e.g. chemical and biological warfare agent detection/identification), genomics, diagnostics, and other molecular/cell biological areas, such as cell isolation/sorting, microstructural cell analysis, etc. In accordance with the invention, the PSc materials have at least a PSc substrate, which substrate has a porous texture, modified with at least one recognition element. The PSc substrate is modified with a recognition element for interaction with a target analyte (i.e., the compound of interest to be detected). The recognition element typically will, but may not always, modify the PL response of the PSc substrate by producing a λ shift and/or change in the PL intensity as compared to the PSc substrate free of the recognition element. A PSc modified with such recognition elements ("PSc/RE") can interact with a target analyte so that a wavelength shift and/or change in PL intensity relative to the PL response for PSc/RE is produced, hereinafter referred to simply as, modulation of the PL response or PL modulation, for brevity.

PSc Substrate

Preferably, the PSc substrate is comprised of silicon. However, the PSc substrate may comprise any semiconductor material composition, which has photoluminescence properties when made porous. For example, such semiconductor material compositions may include, without limitation, cadmium, copper oxide, germanium, gallium, gallium arsenide, selenium, silicon, silicon carbide, silicon dioxide, silicon gallium phosphide and combinations thereof. The selected semiconductor material compositions may also incorporate a dopant, including, for example, without limitation, erbium, boron, phosphorous, copper, phosphors of the lanthanides series, including ytterbium, holmium and thulium, and combinations thereof. Also, the selected semiconductor material compositions may be processed with another compound, including, for example, without limitation, a halogen, such as bromine, to modify the emission wavelength (Bressers et al *J Electro-analytical Chemistry*, 406:131;1996). For ease of discussion, it should be understood that "PSc" includes, without limitation, any semiconductor material composition, such as those described above for illustrative purposes.

PSc Structures

By "porous" or "porous texture" we mean any perturbation, such as depressions, protrusions or combinations thereof, in or on the semiconductor material that contributes to the total surface area of the semiconductor material. Examples of depressions include, without limitation, pores, pits, cavities, craters, trenches, furrows and combinations thereof. Examples of protrusions include, without limitation, ridges, bumps, bulges, domes, spikes, mounds, mounts and combinations thereof. For example, without limitation, such perturbations can be in the form of an ordered honeycomb pore structure comprised of cylindrical or polygonal shaped pores or a more random pore structure that is coral-like or sponge-like.

The shape and geometry of the semiconductor material's perturbations can be diverse. The depressions can range from regularly-defined shapes and geometries to irregularly-defined shapes and geometries and combinations thereof. Also, the protrusions can range from regularly-defined shapes and geometries to irregularly-defined shapes and geometries. Regularly-defined shapes include, without limitation, circular, semi-circular, ellipsoidal, semi-ellipsoidal, polygonal, square, rectangular, triangular, rhomboidal, trapezial and trapezoidal shapes. Irregularly-defined shapes include, without limitation, blends of the aforementioned perturbation shapes. Also, for example, without limitation, the 3-dimensional (3-D) geometry of the perturbations can range from regularly-defined 3-D geometries to irregularly-defined 3-D geometries. Regularly-defined 3-D geometries include, without limitation, cylindrical, conical, cubical, parallelepipedal, polyhedral, rhombohedral, ellipsoidal, helical, spherical, ovoidal, and pyramidal shapes. Irregularly-defined 3-D geometries include, without limitation, blends of the aforementioned shapes. In any case, such perturbations in the semiconductor material result in an increased surface area of PSc substrate.

The overall geometric shape of the PSc substrate may be in the form of a film or wafer or have a 3-D structure, relative to a film or wafer. By "3-D structure" we mean that the geometry of the PSc substrate, whether alone or in combination with a supporting core of a non-PSc material, can range from a regularly-defined geometric shape to an irregularly-defined shape and combinations thereof. Examples of regularly-defined shapes include, without limitation, spheres, semi-spheres, ellipsoids, semi-ellipsoids, cylinders, ovoids, semi-ovoids, rods, disks, cones, cubes, parallelepipeds, polyhedrons, rhombohedrons and pyramids. Examples of irregularly-defined shapes include, without limitation, blends of the aforementioned PSc substrate shapes. For ease of discussion, reference to "PSc structure(s)" herein will mean, without limitation, PSc substrate(s), which are in the form of a film or wafer, or which have at least one of the types of the geometric shapes and porous texture described above for illustrative purposes.

FIGS. 2 to 5 are illustrative of just a few of the surface perturbations used to enhance the performance of the PSc substrate in the invention. It will be apparent to those skilled in the art that there can be a wide array of perturbations that can be developed in or on the PSc substrate. As discussed more fully below, regardless of the particular shape or geometry of such perturbations, it is believed that these perturbations are a contributing factor to the PL intensity ultimately produced by the PSc material. Further, without being bound by theory, it is believed that the projections of the perturbations are a contributing factor to the PL intensity.

In accordance with the preferred embodiments of the invention, the PSc substrate has a porous texture on one or more surfaces of and/or throughout its structure.

The actual form and/or size of the PSc structure is dependent on the particular application in which the PSc structures are used. There are some applications in which a planar PSc structure is desirable and others where a 3-D PSc structure is more desirable. When the PSc structure is a 3-D structure, the average diameter or other largest average dimension is preferably in the range of from about 100 nm to about 1 mm. More preferably, the 3-D PSc structures have an average diameter or other largest average dimension in the range of from about 100 nm to about 500 microns. Most preferably, the 3-D PSc structures have an average diameter or other largest average dimension in the range of from about 1 micron to about 500 microns. Furthermore, when the PSc structure is a 3-D PSc structure, the PSc structures are adaptable to a variety of photodetection device configurations, especially where reduced size is desired for such a photodetection device. For example, in a capillary flow-through column, the diameter of the 3-D PSc structures would preferably be in the range of from about 5 microns to about 15 microns.

The PSc structures of the present invention, when irradiated with at least one wavelength of electromagnetic radiation, in the range of from about 100 nm to about 1000 nm, of sufficient power, produce luminescent radiation in the range of from about 200 nm to about 800 nm, preferably in the range of from about 350 nm to about 700 nm, and more preferably in the range of from about 450 nm to about 650 nm.

The PSc structures of the invention can be formed by a variety of procedures that will be apparent to those skilled in the art. Planar or wafer-like semiconductor material is commercially available, for example from Silicon Quest (Santa Clara, Calif., USA). Also, for example, non-porous silicon spheres can be produced by the process described in WO98/25090 (Ishikawa, Jun. 11, 1998). Further, a planar or wafer-like semiconductor material can be mechanically fragmented to produce fine particles having irregularly-defined geometries. In any case, regardless of the procedure selected to produce the semiconductor material, such material can be made porous by a variety of procedures known to those skilled in the art, such as those discussed more fully below, for illustrative purposes.

After a substantially nonporous semiconductor structure is formed, the semiconductor structure is made porous. The desired porous texture can be produced by using a number of techniques known to those skilled in the art. For example, without limitation, a porous texture can be produced by epitaxial deposition or lithography (Canham *Appl Phys Left* 57:10:1046–1048; 1990), chemical etching (Sailor et al *Adv Mater* 9:10:783–793; 1997), anodic etching in HF solutions (Canham *Appl Phys Lett* 57:10:1046–1048; 1990), spark-erosion (Kurmaev et al *J. of Physics Condensed Mater* 9:2671; 1997), laser ablation (Yamada et al Japanese *J Appl. Physics Part I—Regular Papers Short Note* 35:1361; 1996), ion beam milling (Schmuki et al *Phys Rev Lett* 80:18:4060–4063; 1998), and controlled annealing and etching (Tsai et al *Appl Phys Lett* 60:170; 1992). Also, it will be apparent to those skilled in the art that procedures used for developing a porous texture on a substantially planar semiconductor material may require some modifications. For example, 3-D semiconductor structures may require suspension in an inert gaseous or liquid environment in order that all surfaces be in contact with a high energy source, etching solution or other means to produce the desired PSc structure. Also, the time required for etching may also be much shorter for 3-D PSc structures.

Also, the PSc structures can be formed with a core and a PSc material applied to the core as a coating. Examples of suitable core materials include, without limitation, glass, plastic, ceramics, zeolites, metals, a different semiconductor material and combinations thereof. The core material may be selected, for example, to impart a desired buoyant density for a particular application. Such a core is likely to be more suitable when the structures have a larger diameter. In the case of a single semiconductor coating, preferably such a coating should be sufficiently thick to produce the desired porous texture.

A coating of a PSc material may be supported on a core of non-PSc material by a variety of techniques. For example, a substantially nonporous coating of silicon dioxide or silicon carbide can be produced by controlled oxidation (Fauchet *J Luminescence* 70, 294; 1996) or by high temperature pyrolysis techniques (Liu et al *Solid State Communications* 106:211; 1998). Thereafter, the semiconductor material may be converted to a porous state, thereby transforming the coated core material to a PSc structure. Alternatively, a PSc structure may be formed concurrently with the coating's application to the surface of the core material. Also, it may be desirable to have multiple layers of differing PSc compositions on the supporting core material.

Recognition Element

In the present invention, the PSc structure is modified with at least one recognition element, and preferably, multiple recognition elements. For ease of reference, a PSc structure modified with at least one recognition element hereinafter will be referred to as "PSc/RE". By "modified", we mean that a recognition element communicates with the PSc structure such that a PL response of the PSc/RE is modulated when a target analyte interacts with the recognition element(s) of the PSc/RE. One example of such modification is covalent bonding of a recognition element to the PSc structure. However, a direct or physical bond may not be required. There may be a proximate association of the recognition element with the PSc structure sufficient to support electron or energy transfer between the recognition element and the PSc structure. Typically, but not necessarily always, the PSc/RE will exhibit an enhanced PL response relative to the PL response for the PSc structure prior to modification with the recognition element.

Generally, recognition elements can be organic, inorganic, biomolecular moieties and combinations thereof.

Preferably, recognition elements are biomolecular moieties. Examples of biomolecular moieties that may be used as recognition elements are, without limitation, natural or synthetic proteins, nucleic acids, oligonucleotides, lectins, carbohydrates, glycoproteins and lipids, which interact with a target analyte. Proteins are preferred as recognition elements. Examples of suitable proteins are, without limitation, immunoglobulins, such as polyclonal and monoclonal antibodies, and enzymes. Preferred proteins as recognition elements are immunoglobulins and enzymes. Examples of suitable nucleic acids include single-stranded DNA and double-stranded DNA. A recognition element may also have a redox moiety attached thereto. Examples of redox moieties include, without limitation, transition metals and complexes thereof, and co-enzymes such as NAD(H) or NADP(H). The redox moiety may be either an electron donor or acceptor to alter PL intensity on binding of a target analyte to the recognition element.

Examples of inorganic moieties that may be used as recognition elements are, without limitation, doped or un-doped crystalline inorganic compounds, for example, linear allotropes of carbon, including carbynes and diamond crystals.

Examples of organic moieties that may be used as recognition elements are, without limitation, intrinsically conductive polymers ("ICP"), such as polyaniline, and polymer electrolytes, such as poly[ethylene oxide], advantageously with a lithium triflate dopant.

Modification of the PSc structure with a recognition element may be enhanced by using a surfactant to reduce the surface tension of a solution containing the recognition element. Such agents include, without limitation, alcohols and detergents, at a concentration sufficient to reduce the surface tension of the solution without adversely affecting the recognition element's structure or the efficacy of the recognition element or PSc/RE.

Target Analyte

A target analyte interacts with the PSc/RE, such that the PL response is modulated. By "interact", we mean that the target analyte communicates with the recognition element, such that a PL response of the PSc/RE is modulated. Examples of such interactions include, without limitation, covalent bonding, hydrogen bonding, Van der Waal's/dipole bonding and affinity binding. However, a direct or physical bond may not be required. There may be a proximate association of the target analyte with the PSc/RE sufficient to support electron or energy transfer between the target analyte and the PSc/RE.

A target analyte may be an organic, inorganic or biomolecular compound or moiety. Examples of target analytes include, without limitation, (1) antigenic compounds from which antibodies can be produced including, for example, without limitation, toxins, metabolic regulators, microorganisms, such as bacteria, viruses, yeast, fungi and microbial spores, and animal and plant cells/tissue elements; (2) specific substrates for enzymes including, for example, without limitation, metabolites, nerve agents, pesticides, insecticides; (3) complementary oligonucleotide sequences; (4) single-stranded DNA and RNA; and (5) ligands to hormonal receptors and lectins.

Upon binding of a target analyte to a specific recognition element on a PSc structure, the PL response of the PSc structure is modulated relative to that of the PSc/RE PL response. Preferably, the PL response is enhanced relative to that of the PSc/RE PL response. It is possible to determine modulation of the PL response in a real- or near real-time manner.

Stabilization/Activation of PSc Structure

In order to promote stable and efficient modification of the PSc structure with a recognition element, the surface of the PSc structure is first stabilized against uncontrolled oxidation.

One such stabilization procedure is oxidation using, for example, without limitation, thermal oxidation (Petrova-Koch et al *Appl Phys Lett* 61:943;1992), chemical oxidation (Nakajima et al *Appl Phys Lett* 61:46;1992, Lee et al *Mater Res Soc Symp Proc* 338:125;1995, Anderson et al *J Electrochem Soc* 140:1393;1993, Duvault-Herrera et al *Colloids Surf* 50:197;1990, Yamana et al *Electrochem Soc* 137:2925;1990, Li et al *Appl Phys Lett* 62:3192;1993), and ozone oxidation processes (Janshoff et al *J Am Chem Soc* 120:12108;1998). These processes generate reactive hydroxyl groups. Chemical oxidation can be achieved, for example using peroxide, dimethylsulfoxide (DMSO) or iodine chips.

Covalent Bonding

As noted above, in one preferred embodiment of the invention, the PSc structure may be modified with a recognition element by covalent bonding. For example, a recognition element may be covalently bonded to a PSc structure using one or more linkers. Linkers can provide a transition in functionality of reactive groups on the PSc structure to an appropriate functional group for attachment of a recognition element. Also, among other functions, linkers can provide a spacer to reduce potential steric hindrance problems arising from a bulky target analyte seeking to interact with a recognition element and/or PSc/RE.

Preferably, a recognition element is covalently bonded to linker(s) so that the recognition element and/or PSc/RE can interact with the target analyte with maximum efficacy. For example, some biomolecular moieties, such as certain antibodies, linked through their sulfhydryl groups will exhibit good binding ability for a target analyte. However, when such antibodies are attached to a linker through their amine groups, they may have a reduced capacity for interaction with a target analyte.

Primary Linker

In another preferred embodiment of the invention, a primary linker is attached to hydroxyl groups arising from oxidation of the PSc. One example of a primary linker is a substituted silane. An example of a suitable substituted silane is, without limitation, glycidoxypropyltrimethoxysilane. This primary linker provides a direct link between the hydroxyl groups of an oxidized PSc structure and an amine group of a recognition element. Other suitable primary linkers are hydrosilylated alkenes and alkynes.

Other linkers which are reactive with hydroxyl groups of the oxidized PSc and amine groups of the recognition element will be apparent to those skilled in the art. It will be understood that a linker may be selected to react with a functional group, other than an amine group, of a recognition element. Other recognition element functional groups include sulfhydryl, carbohydrate or carboxyl groups. It will also be understood by those skilled in the art that other linkers, which are reactive with non-hydroxyl groups (produced by other PSc stabilization techniques) and the functional group of the selected recognition elements, may be selected for bonding to a PSc structure.

Primary & Secondary Linkers

In another preferred embodiment, a primary linker is attached to hydroxyl groups arising from oxidation of the PSc and then a secondary linker is attached to the primary linker. One example of a primary linker that may be used in combination with a secondary linker is a substituted silane. An example of such a suitable substituted silane is, without limitation, aminopropyltriethoxysilane. Examples of suitable secondary linkers are, without limitation, homo- and/or hetero-bifunctional cross-linking agents and hydrosilylated alkenes and alkynes.

Because secondary linkers typically cannot bind directly to the PSc, the primary linker provides a direct interaction between the PSc structure and a reactive group of the secondary linker. Accordingly, the primary and secondary linkers combined provide an indirect interaction between the PSc and the recognition element.

Also, using secondary linkers with primary linkers, provides even longer spacers compared to the primary linker alone. Consequently, among other functions, primary and secondary linkers combined can reduce potential steric hindrance problems arising from an unusually bulky target analyte seeking to interact with a recognition element and/or PSc/RE. Secondary linkers can also provide a greater flexibility in selection of a functional group which is reactive with, for example, an amine, sulfhydryl, carbohydrate or carboxyl group of a recognition element.

Homo-bifunctional cross-linking agents have two similar reactive groups. For example, a homo-bifunctional cross-linking agent can have a first reactive group that can interact with an amine group of a primary linker and a second reactive group that can interact with an amine group of a recognition element. Examples of homo-bifunctional cross-linking agents are, without limitation, glutaraldehyde, disuccinimidyl suberate, its sulfonated analog, and bis (sulfosuccinimidyl) suberate.

Hetero-bifunctional cross-linking agents have two different reactive groups. For example, a hetero-bifunctional cross-linking agent can have a first reactive group that can interact with an amine group of a primary linker and a second reactive group that can interact with a sulfhydryl group of a recognition element. Examples of hetero-bifunctional cross-linking agents are succinimidyl 4-(N-maleimidomethyl)-cyclohexane-1-carboxylate and its sulfonated analog, 4-(4-N-maleimidophenyl) butyric acid hydrazide·HCl, and 4-(p-azidosalicylamido)butylamine.

Other linkers which are reactive with hydroxyl groups of the PSc and functional groups of the selected recognition elements will be apparent to those skilled in the art. It will also be understood by those skilled in the art that other linkers, which are reactive with non-hydroxyl groups (produced by other PSc stabilization techniques) and the functional groups of the selected recognition elements, may be selected for bonding to a PSc structure.

PSc/RE Interaction with Target Analyte

Using a recognition element having a specific affinity for a target analyte will substantially reduce the likelihood that non-target compounds in the sample mixture will interact with the recognition element. Also, using a recognition element that facilitates a characteristic modulation in the PL response of the PSc/RE when the target analyte interacts with the PSc/RE will substantially reduce the likelihood of "false" modulations produced by non-target compounds. Accordingly, the effect, if any, of non-target compounds in a sample mixture on the PL response can be significantly reduced.

Likewise, in a preferred embodiment where the recognition element has a specific affinity for the target analyte, the target analyte will preferentially interact with the recognition element rather than with the PSc structure.

The PSc structures of the present invention may be exposed to a sample containing a target analyte in a number of different applications, examples of which are provided below. In some applications, it may be desirable to suspend the PSc/RE in a suitable carrier to allow for increased interaction of the PSciRE with the target analyte. Using contacting means that will be apparent to those skilled in the art, the carrier/PSc/RE mixture can then enhance the extent of contact between an unknown composition or organism, whether plant or animal, containing the target analyte as well as non-target compounds. Such a carrier may include an agent to reduce the carrier's surface tension, increase its hydrophilicity or increase its hydrophobicity, as appropriate. Such agents include, without limitation, alcohols, detergents and organic solvents at a concentration sufficient to achieve the desired effect without adversely affecting the efficacy of the PSc/RE.

Linker Treatment

Linkers may be treated to (a) enhance the preferential interaction between the linker and the recognition element, and/or (b) inhibit interaction between unassociated linkers (i.e., linkers not associated with a recognition element but still linked to the PSc) and non-target compounds and/or target analytes.

Preferential interaction between the linker and the recognition element may be enhanced by providing a stronger association between the recognition element and the linker and/or by orienting the recognition element for better interaction with a target analyte.

Interaction between unassociated linkers and non-target compounds and/or target analytes may be inhibited by blocking reactive groups of unassociated linkers, and/or by attaching to the reactive groups of unassociated linkers a moiety that has an affinity for a compound not present in a target analyte composition.

Non-limiting examples of such linker treatments, discussed more fully below, are (1) immunoglobulin binding proteins, (2) a biotin reactive agent, and (3) blocking solutions, e.g. amine buffer solutions.

Immunoglobulin Binding Protein Treatment

In one embodiment, linkers attached to a PSc structure may be treated with an immunoglobulin binding protein ("IgBP"), (e.g., a Protein A, Protein G or Protein L). IgBP has a specific affinity for a selected portion of an antibody known as the Fc domain. Consequently, because all antibodies have an Fc domain, an antibody recognition element will preferentially interact with IgBP. Therefore, when the antibody recognition element is contacted with the IgBP-treated linker attached to the PSc structure, the Fc domain of the antibody recognition element interacts with the IgBP-treated linker.

Because the IgBP has a specific affinity for the Fc domain of antibodies, IgBP treatment of the linkers reduces binding of non-target compounds and target analytes to the linkers, assuming such compounds and analytes have no Fc domain, of course. Another advantage of IgBP linker treatment is that the antibody recognition elements are properly oriented for antigen target analyte interaction. Specifically, the Fc domain of the antibody recognition element binds to the IgBP, while the Fab domains of the antibody remain available for antigen interaction.

Biotin Reactive Agent Treatment

In another embodiment, linkers attached to a PSc structure may be treated with a biotin reactive agent ("BRA"), which has an affinity for biotin. Non-limiting examples of biotin reactive agents are streptavidin, neutravidin and avidin. In this case, the desired recognition elements are treated with biotin to produce a biotinylated recognition element. Accordingly, when the biotinylated recognition element is contacted with the BRA-treated linker attached to the PSc structure, the biotin moiety on the recognition element will preferentially interact with the BRA.

Because the BRA has an affinity only for biotin, BRA treatment of the linkers reduces binding of non-target compounds and target analytes, which do not have biotin moieties, to the linkers. Another advantage of the BRA linker treatment is a slightly stronger association between the recognition elements and the linkers attached to the PSc structure. Furthermore, the biotinylated recognition element is still capable of interacting with a target analyte.

Blocking Solution Treatment

In a further embodiment, the PSc/RE may be treated with a blocking solution to specifically block reactive groups of unreacted linkers against binding with non-target compounds and target analytes. Blocking solutions include, for example, amine buffers, such as a glycine-buffered solution. Any unreacted linker amine reactive groups are thus blocked by the amine groups of the blocking solution. However, the blocking solution does not block the receptor or acceptor region of the recognition element, which remain available for target analyte interaction.

PL Detection

An embodiment of an apparatus 10 which may be used to detect PL is illustrated schematically in FIG. 1. A sample 19 is placed on a sample holder 20. Light at a predetermined wavelength is directed at the sample from an argon ion laser 12. Light passes through a narrow band filter 14, which reduces any noise radiation caused by gas fluorescence in the chamber of the laser 12. The filter 14 absorbs radiation of all wavelengths except for light having the predetermined wavelength. A chopper 16 is used to eliminate any constant noise caused by peripheral light radiation, if any. The chopper 16 provides time modulation of the laser radiation with a certain frequency, which enables separation of a PL signal from the background noise at an amplifier 42. After the chopper 16, light passes through a lens 17 to the sample 19. Light radiation scattered by the sample 19 is directed through lenses 18 and a broad band filter 22 to an input slit 32 and a mirror 34 in a monochromator 30. The broad band filter 22 absorbs radiation of wavelengths outside a predetermined range and thus reduces laser radiation reflected from optical elements of the apparatus 10.

A rotating diffraction grating 36 located inside the monochromator 30 allows for angular separation of different wavelengths $\lambda_1$, $\lambda_2$, $\lambda_3$ and $\lambda_4$ of a scattered beam spectrum to a mirror 35. Rotation of the grating 36 is controlled by a computer 40 to separate different spectral components of an output slit 33 of the monochromator 30. Intensities of spectral components $\lambda_1$, $\lambda_2$, $\lambda_3$ and $\lambda_4$ are recorded by a photodiode 38. The signals are amplified by an amplifier in the photodiode 38 and the amplifier 42 and acquired by the computer 40. All measurement processes are controlled by the computer 40.

Quantifying the concentration of a target analyte may be determined using a calibration curve of PL intensity for known concentrations of target analyte or using different concentrations of a recognition element.

Applications

The PSc/RE structures may be used alone or in combination with a wide array of devices used to support a diversity of applications, including, without limitation, biotechnology, such as biosensors for medical, environmental, industrial and defense applications (e.g. chemical and biological warfare agent detection/identification), genomics, diagnostics, and other molecular/cell biological areas, such as cell isolation/sorting, micro-structural cell analysis, etc.

For example, there is an increasing demand for high throughput screening devices for genomics and diagnostic screening. In the invention, separate batches of PSc/RE structures having different recognition elements can be prepared and then incorporated and/or blended in predetermined ratios into "biochips" or microcapillary array configurations, discussed more fully below. Samples can be contacted with immobilized or suspended PSc/RE structures in such configurations and interaction with a target analyte can be readily determined as discussed above. Advantageously, 3-D PSc structures can be used with conventional hardware, for example automated microvolume dispensers, to form analyte detection and/or identification micro-arrays.

In one embodiment, PSc/RE structures are advantageously used on a photon detection "biochip" where a variety of recognition elements can be placed in different regions of the same device. To date, the practical issue of having multiple but different recognition elements on a small semiconductor chip has not yet been satisfactorily met due to 1) insufficient signal intensity for detection of target analyte interaction, and 2) the difficulty of having multiple but different recognition elements deposited within a small area. Small 3-D PSc structures, described above, are particularly suitable for this type of application. A sample containing an unknown compound, but which is suspected of being one of a number of compounds, can thus be identified by contacting a biochip having recognition elements for the suspected compounds. When a region of the biochip produces a modulated PL response, the compound is identified by the recognition element used in that particular area.

PSc/RE structures can also be arranged in micro-arrays, each separate area containing a specified amount of a PSc/RE structure, and each separate area having a specificity for a different target analyte, or the same target analyte, such that binding of the target analyte(s) results in PL modulation, for example in a unique pattern (pattern recognition).

In another embodiment, PSc/RE structures can be used as a packing in a micro-capillary column which can allow for the flow-through of carrier liquids containing one or more target analytes. The micro-capillary columns could be optically clear to detect PL modulation upon interaction with a target analyte. Parallel or sequential placement of microcapillary columns could be used to detect and identify one or more target analytes. In another configuration, the microcapillary columns could also incorporate fiber optic elements allowing for detection of such PL modulation.

In another embodiment, the target analyte may be found in or on an organism or portion of an organism. By "organism", we mean microbial cells, animal and plant cells and tissues, microbial spores, viruses and the like. For example, without limitation, the target analyte may a bacteria, a virus or a microbial spore. Examples of such target analytes include anthrax spores and *E. coli*, such as *E. coli* 0157 (a causative agent of hamburger disease). PSc/RE structures, which have an affinity for one of such target analytes are contacted with a sample suspected of having such a target analyte or a sample which is being tested for the presence of such a target analyte. In the presence of such a target analyte, one or more recognition elements attach itself to the cell wall or coating through exterior receptors of the cells. Advantageously, these PSc structures have a diameter or largest dimension of about 100 nm to about 1 micron.

It is possible that a PSc/RE could be injected or otherwise inserted in an organism for detection of an internal or intracellular target analyte. It is also possible that an organism could be induced to ingest or that an organism actively ingests, for example by phagocytosis, a PSc/RE for detection of an internal or intracellular target analyte.

The following non-limiting examples of embodiments of the present invention that may be made and used as claimed herein are provided for illustrative purposes only.

EXAMPLES

Example 1-Production of PSi Particles

Small particles of silicon were produced by mechanical fragmentation of planar n-type silicon obtained from Silicon Quest (Santa Clara, Calif., USA). Particles were produced by mechanical fragmentation using a mortar and pestle to produce granular particles of an irregular shape. This procedure produced particles with a wide range of sizes. Particles with a diameter, or other largest dimension, between 30 and 1000 μm were selected by mechanical sieving through a polymer mesh membrane. The particles were analyzed by BET (Brunnauer-Emmett-Toller) analysis.

BET analysis was made using a MICROMERITICS ASAP 2000™ instrument (Norcross, Ga., USA). Empty sample tubes were weighed and then reweighed after transfer of samples to the sample tubes. The samples were placed on the instrument and degassed by heating to 180° C. and placing under vacuum overnight. After degassing, the samples were removed from the instrument and re-weighed. The samples were then analyzed and re-weighed after analysis. This last recorded weight was used in analysis calculations. Volume absorbed points were taken from 0.05 to 0.3 relative pressure.

The BET surface area of the particles, based on a 5-point BET surface area analysis, was determined to be $0.1724 \pm 0.0016$ m$^2$/g with a correlation coefficient of 0.999871.

The silicon particles were made porous, with a random pore distribution, using a chemical etching method. The silicon particles were suspended in an acidic solution of 70% nitric acid, 50% hydrofluoric acid and water in a 1:4:1 ratio for 60 seconds at room temperature. The reaction produced hydrogen gas and caused violent mixing of the solution, so that no additional mixing was required to keep the particles in suspension. The etching reaction was stopped by dilution of the acidic solution with water.

The resultant PSi particles were analyzed using Scanning Electron Microscopy (SEM), BET and BJH (Barett-Joyner-Halenda) analysis.

Figure 2:
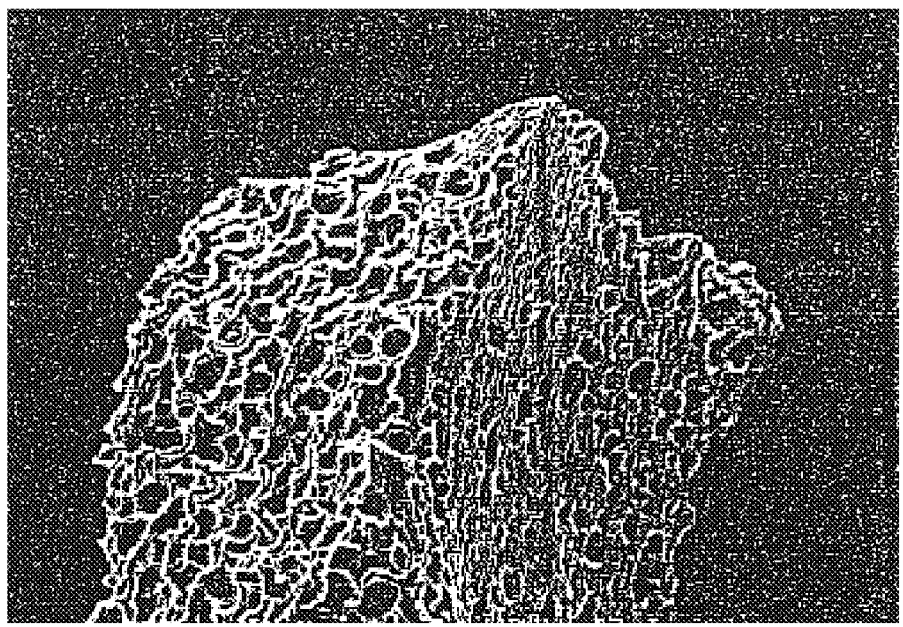
FIG. 2 is a scanning electron micrograph of a porous silicon particle produced in Example 1, at a magnification of 300X.
Figure 3:
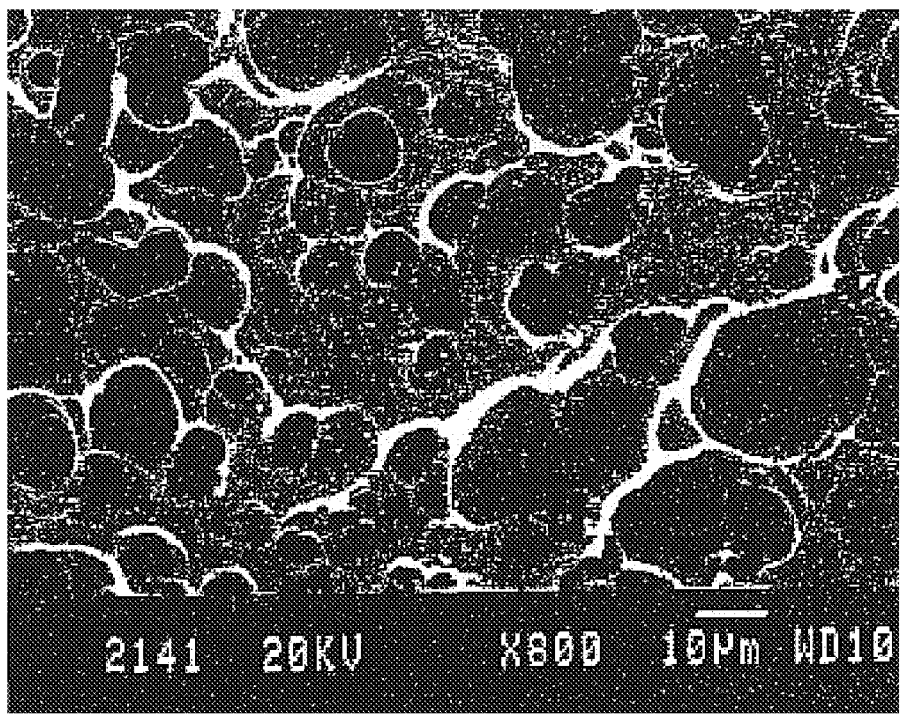
FIG. 3 is a scanning electron micrograph of a porous silicon particle produced in Example 1, at a magnification of 800X.

FIGS. 2 and 3 are SEM micrographs of porous silicon (PSi) particles produced by the method of this example.

BET and BJH analyses were made using a MICROMERITICS ASAP 2000™ instrument (Norcross, Ga., USA) using the procedure described above. Adsorption and desorption points were taken from 0.01 to 0.99 relative pressure.

The BET surface area of the particles, based on a 5-point BET surface area analysis, was determined to be $1.8559 \pm 0.0124$ m$^2$/g with a correlation coefficient of 0.999926. Accordingly, the surface area of the particles was increased by approximately 11 times using the above-described etching technique. Based on a total pore volume determined by BET divided by pore area determined by BET, the average pore diameter was 4.77075 nm.

Results of the BJH adsorption pore distribution analysis are listed below in Table 1.

TABLE 1

| Pore Diameter Range nm | Average Diameter (nm) | Incremental Pore Volume (cm$^3$/g) | Cumulative Pore Volume (cm$^3$/g) | Incremental Pore Area (m$^2$/g) | Cumulative Pore Area (m$^2$/g) |
| --- | --- | --- | --- | --- | --- |
| 210.62–295.20 | 238.98 | 0.001559 | 0.001559 | 0.026 | 0.026 |
| 103.15–210.62 | 123.50 | 0.000071 | 0.001631 | 0.002 | 0.028 |
| 81.15–103.15 | 89.50 | 0.000027 | 0.001657 | 0.001 | 0.030 |
| 40.42–81.15 | 48.22 | 0.000077 | 0.001734 | 0.006 | 0.036 |
| 27.18–40.42 | 31.20 | 0.000049 | 0.001784 | 0.006 | 0.042 |
| 20.35–27.18 | 22.76 | 0.000031 | 0.001814 | 0.005 | 0.048 |
| 16.32–20.35 | 17.87 | 0.000041 | 0.001855 | 0.009 | 0.057 |
| 13.58–16.32 | 14.69 | 0.000026 | 0.001881 | 0.007 | 0.064 |
| 11.31–13.58 | 12.23 | 0.000036 | 0.001917 | 0.012 | 0.076 |
| 10.55–11.31 | 10.90 | 0.000013 | 0.001930 | 0.005 | 0.080 |
| 8.09–10.55 | 8.97 | 0.000079 | 0.002009 | 0.035 | 0.116 |
| 6.65–8.09 | 7.22 | 0.000067 | 0.002076 | 0.037 | 0.153 |
| 5.64–6.65 | 6.05 | 0.000156 | 0.002233 | 0.103 | 0.256 |
| 4.85–5.64 | 5.18 | 0.000165 | 0.002397 | 0.127 | 0.383 |
| 4.23–4.85 | 4.49 | 0.000224 | 0.002622 | 0.200 | 0.583 |
| 3.72–4.23 | 3.94 | 0.000229 | 0.002851 | 0.232 | 0.816 |
| 3.29–3.72 | 3.48 | 0.000221 | 0.003072 | 0.255 | 1.070 |

TABLE 1-continued

| Pore Diameter Range nm | Average Diameter (nm) | Incremental Pore Volume (cm³/g) | Cumulative Pore Volume (cm³/g) | Incremental Pore Area (m²/g) | Cumulative Pore Area (m²/g) |
|---|---|---|---|---|---|
| 2.93–3.29 | 3.08 | 0.000193 | 0.003264 | 0.250 | 1.320 |
| 2.61–2.93 | 2.74 | 0.000158 | 0.003422 | 0.230 | 1.550 |
| 2.32–2.61 | 2.44 | 0.000128 | 0.003550 | 0.210 | 1.760 |
| 2.06–2.32 | 2.17 | 0.000116 | 0.003666 | 0.214 | 1.974 |
| 1.82–2.06 | 1.92 | 0.000095 | 0.003762 | 0.198 | 2.172 |
| 1.72–1.82 | 1.77 | 0.000040 | 0.003802 | 0.092 | 2.264 |

Results of the BJH desorption pore distribution analysis are listed below in Table 2.

TABLE 2

| Pore Diameter Range (nm) | Average Diameter (nm) | Incremental Pore Volume (cm³/g) | Cumulative Pore Volume (cm³/g) | Incremental Pore Area (m²/g) | Cumulative Pore Area (m²/g) |
|---|---|---|---|---|---|
| 278.56–294.91 | 286.27 | 0.001155 | 0.001155 | 0.016 | 0.016 |
| 87.25–278.56 | 103.77 | 0.000504 | 0.001659 | 0.019 | 0.036 |
| 62.76–87.25 | 71.02 | 0.000040 | 0.001700 | 0.002 | 0.038 |
| 35.37–62.76 | 41.80 | 0.000065 | 0.001765 | 0.006 | 0.044 |
| 24.52–35.37 | 27.97 | 0.000050 | 0.001815 | 0.007 | 0.051 |
| 20.20–24.52 | 21.93 | 0.000033 | 0.001849 | 0.006 | 0.057 |
| 16.09–20.20 | 17.66 | 0.000038 | 0.001887 | 0.009 | 0.066 |
| 12.69–16.09 | 13.98 | 0.000041 | 0.001928 | 0.012 | 0.078 |
| 10.89–12.69 | 11.65 | 0.000026 | 0.001954 | 0.009 | 0.087 |
| 9.91–10.89 | 10.35 | 0.000024 | 0.001978 | 0.009 | 0.096 |
| 7.81–9.91 | 8.60 | 0.000059 | 0.002037 | 0.027 | 0.123 |
| 6.40–7.81 | 6.95 | 0.000075 | 0.002112 | 0.043 | 0.166 |
| 5.36–6.40 | 5.78 | 0.000096 | 0.002208 | 0.067 | 0.233 |
| 4.57–5.36 | 4.90 | 0.000124 | 0.002332 | 0.101 | 0.334 |
| 3.95–4.57 | 4.21 | 0.000184 | 0.002515 | 0.174 | 0.508 |
| 3.44–3.95 | 3.66 | 0.000222 | 0.002738 | 0.243 | 0.752 |
| 3.01–3.44 | 3.20 | 0.000270 | 0.003008 | 0.337 | 1.089 |
| 2.65–3.01 | 2.81 | 0.000262 | 0.003270 | 0.373 | 1.462 |
| 2.29–2.65 | 2.44 | 0.000172 | 0.003442 | 0.282 | 1.744 |
| 2.00–2.29 | 2.12 | 0.000120 | 0.003562 | 0.226 | 1.970 |
| 1.74–2.00 | 1.85 | 0.000101 | 0.003663 | 0.219 | 2.189 |

The above results illustrate that there are no inkwell or other retaining pores in the sample analyzed. The BJH cumulative adsorption pore volume of pores having a pore diameter between 1.7 and 300 nm was 0.003802 cm³/g, while the BJH cumulative desorption pore volume was 0.003663 cm³/g. The BJH cumulative adsorption surface area of pores having a pore diameter between 1.7 and 300 nm was 2.2636 m²/g, while the BJH cumulative desorption surface area was 2.1889 m²/g.

Based on the total pore volume as determined by BJH divided by pore volume as determined by BJH, the average adsorption and desorption pore diameters were determined to be 6.71859 nm and 6.69407 nm, respectively.

The differences in surface area and pore diameter values between BET and BJH analyses appear to be due to the calculation method used for BJH analysis, which assumes that the pores are a bundle of cylinders. However, the SEM micrographs produced show that the porous texture of the particles cannot properly be characterized as a bundle of cylinders. Accordingly, the BET surface area analysis is probably a more accurate determination of the surface area.

Example 2-Production of PSi Particles

PSi particles were prepared as in Example 1, except that the silicon particles were suspended in the acidic solution for 30 seconds. The resultant PSi particles were analyzed by BET analysis.

BET analysis was made using a MICROMERITICS ASAP 2000™ instrument (Norcross, Ga., USA), using the procedure described above. Volume absorbed points were taken from 0.05 to 0.3 relative pressure.

The BET surface area of the particles, based on a 5-point BET surface area analysis, was determined to be 0.6858±0.0039 m²/g with a correlation coefficient of 0.999934. Accordingly, the surface area of the particles was increased by approximately 4 times using the above-described etching technique.

Figure 4:
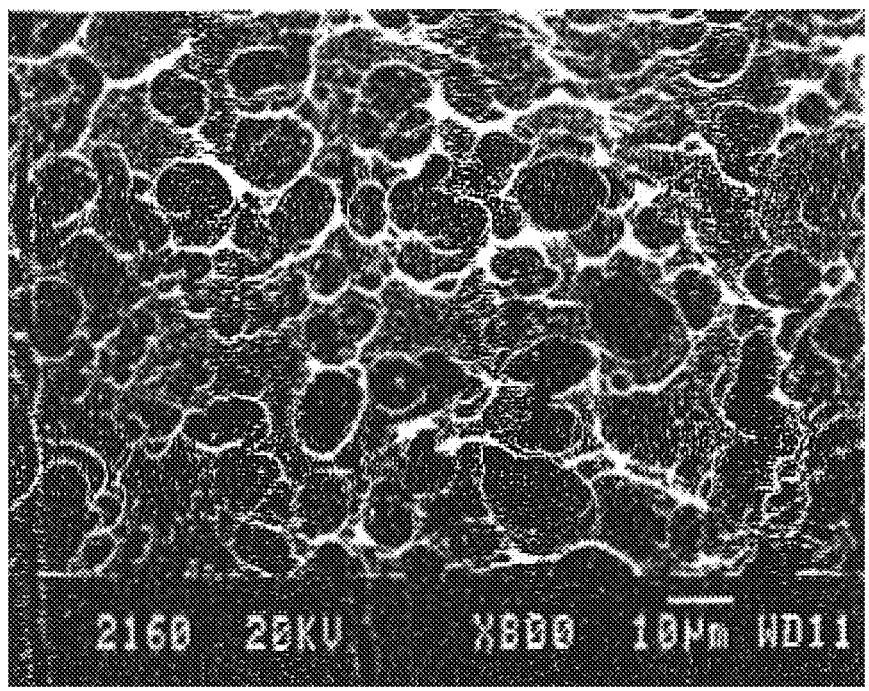
FIG. 4 is a scanning electron micrograph of a porous silicon particle produced in Example 2, at a magnification of 800X.
Figure 5:
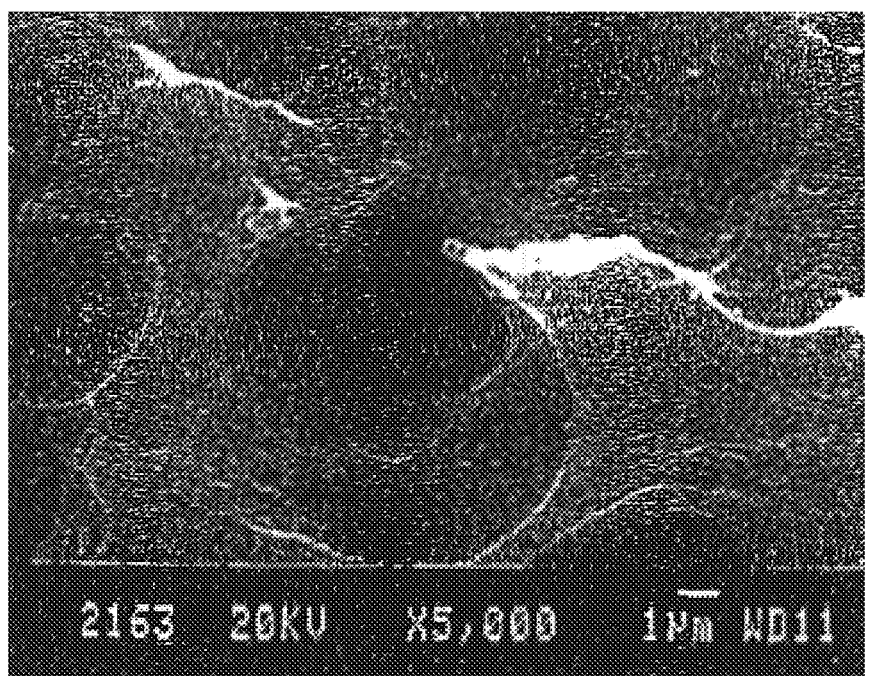
FIG. 5 is a scanning electron micrograph of a porous silicon particle produced in Example 2, at a magnification of 5000X.

FIGS. 4 and 5 are SEM micrographs of PSi particles produced by the method of this example.

Example 3-Oxidation of PSi Particles using Peroxide

PSi particles produced in Example 1 were subjected to chemical oxidation using peroxide. The PSi particles were incubated at room temperature for 1 hour in an aqueous solution of 30% peroxide.

Example 4-Oxidation of PSi Particles using DMSO

PSi particles produced in Example 1 were subjected to chemical oxidation using dimethylsulfoxide (DMSO) alone and a solution of DMSO containing 500 mg/ml of 2,6-di-tert-butyl-4-methylphenol (BHT), a free radical scavenger. The PSi particles were incubated at room temperature for 1 hour in DMSO and 2 hours in the solution of DMSO/BHT.

Example 5-Oxidation of PSi Particles using Iodine Chips

PSi particles produced in Example 1 were subjected to chemical oxidation using iodine chips. The PSi particles were incubated in the presence of iodine chips either (1) in vacuum or (2) in air.

In vacuum, the particles were incubated under vacuum in a vacuum flask containing the iodine chips for 2 hours at room temperature. The particles were then exposed overnight to air at room temperature.

In air, the particles were incubated in a stoppered flask containing iodine chips for 2 hours at room temperature. The particles were then exposed overnight to air at room temperature.

Example 6-Attachment of Primary Linker

Oxidized particles prepared in Example 3 were immersed in a 10% (v/v) solution of 3-glycidoxypropyltrimethoxysilane, a primary linker, in water for 4 hours at 75° C., followed by annealing at 110° C. overnight to form a covalent bond between the 3-glycidoxypropyltrimethoxysilane and the hydroxyl groups on the PSi surface.

Example 7-Attachment of Primary and Secondary Sulfo-SMCC Linkers

Oxidized particles prepared in Example 3 were immersed in a 10% (v/v) solution of aminopropyltriethoxysilane, a primary linker, in water for 4 hours at 75° C., followed by annealing at 110° C. overnight to form a covalent bond between the aminopropyltriethoxysilane and the hydroxyl groups on the PSi surface.

The particles were then immersed in a solution of sulfo-succinimidyl 4-(N-maleimidomethyl)-cyclohexane-1-carboxylate (sulfo-SMCC), a heterobifunctional secondary linker, containing 10 mg sulfo-SMCC per ml of water, for 1 hour at room temperature to form covalent bonds between the primary linker and the secondary linker. After incubation with the sulfo-SMCC solution, the particles were washed with water.

Example 8-Attachment of Primary and Secondary Glutaraldehyde Linkers

Oxidized particles prepared in Example 3 were immersed in a 10% (v/v) solution of aminopropyltriethoxysilane, a primary linker, in water for 4 hours at 75° C., followed by annealing at 110° C. overnight to form a covalent bond between the aminopropyltriethoxysilane and the hydroxyl groups on the PSi surface.

The particles were then immersed in a solution of glutaraldehyde (2.5% in phosphate buffer), a homobifunctional secondary linker, for 1 hour at room temperature to form covalent bonds between the primary linker and the secondary linker. After incubation with the glutaraldehyde solution, the particles were washed with water.

Example 9-Attachment of Primary and Secondary $BS^3$ Linkers

Oxidized particles prepared in Example 3 were immersed in a 10% (v/v) solution of aminopropyltriethoxysilane, a primary linker, in water for 4 hours at 75° C., followed by annealing at 110° C. overnight to form a covalent bond between the aminopropyltriethoxysilane and the hydroxyl groups on the PSi surface.

The particles were then immersed in a solution of bis (sulfosuccinimidyl)suberate ($BS^3$), a homobifunctional secondary linker, at a concentration of 5 mg per ml of water, for 1 hour at room temperature to form covalent bonds between the primary linker and the secondary linker. After incubation with the $BS^3$ solution, the particles were washed with water.

Example 10-Attachment of Antibody Recognition Element

Purified mouse immunoglobulin G (IgG) obtained from Sigma-Aldrich Canada Ltd. (Oakville, Ontario, Canada) was attached to the primary linker (3-glycidoxypropyltrimethoxysilane) of the particles produced in Example 6 by incubation of the IgG, in a phosphate buffered saline solution, at 37° C. for 90 minutes.

Figure 6:
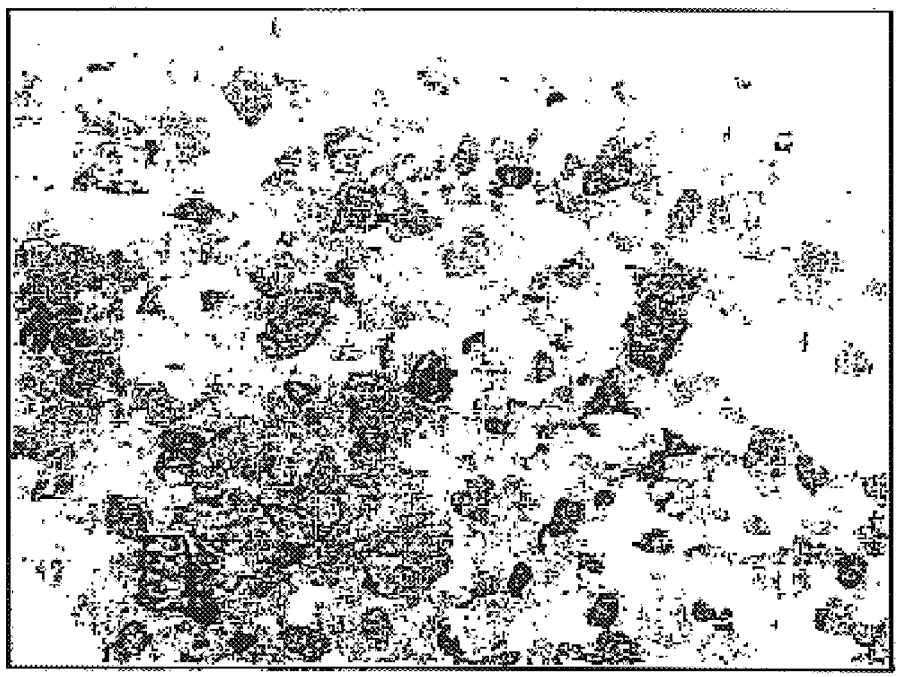
FIG. 6 is an epi-fluorescence micrograph at 200 X magnification, showing the interaction of antigen to PSi particles modified with IgG antibody, discussed in Example 10.

For visualization (microscopy) and quantitative determination (fluorometry) of antibody attachment, a specific anti-mouse IgG F(ab')$_2$ fragment, conjugated with Cy3 fluorescent marker (red fluorescence, obtained from Sigma-Aldrich Canada Ltd.), was contacted with the particles having the IgG antibody attached. The fluorescently-labeled anti-mouse IgG F(ab')$_2$ fragment, in a phosphate buffered saline solution, was incubated in the presence of the particles having the IgG attached for 30 minutes at room temperature. The formation, by affinity binding, of the complex mouse IgG/anti-mouse IgG F(ab')$_2$ fragment was examined by epi-fluorescence microscopy and quantified by fluorometry. FIG. 6 is an epi-fluorescence micrograph (Nikon Diaphot 300 microscope) at 200 X magnification, showing the interaction of antigen to PSi particles modified with IgG antibody.

Example 11-Attachment of Antibody Recognition Element

Purified mouse immunoglobulin G (IgG) obtained from Sigma-Aldrich Canada Ltd. (Oakville, Ontario, Canada) was partially reduced with Tris (2-carboxyethyl) phosphine hydrochloride (TCEP), at room temperature for 25 minutes, to expose the immunoglobulin sulfhydryl groups. The reduced IgG was attached, via the sulfhydryl reactive groups, to the secondary linker (sulfo-SMCC) of the particles produced in Example 7 by incubation of the reduced IgG, in a phosphate buffered saline solution, at 37° C. for 90 minutes.

For visualization (microscopy) and quantitative determination (fluorometry) of antibody attachment, a specific anti-mouse IgG F(ab')$_2$ fragment, conjugated with Cy3 fluorescent marker, was contacted with the particles having the IgG antibody attached. The fluorescently-labeled anti-mouse IgG F(ab')$_2$ fragment, in a phosphate buffered saline solution, was incubated in the presence of the particles having the reduced IgG attached for 30 minutes at room temperature. The formation, by affinity binding, of the complex mouse IgG/anti-mouse IgG F(ab')$_2$ fragment was examined by epi-fluorescence microscopy and quantified by fluorometry, which showed good coverage and distribution of antibody recognition element on PSi particles.

Example 12-Attachment of Antibody Recognition Element

Purified mouse immunoglobulin G (IgG) obtained from Sigma-Aldrich Canada Ltd. was attached to the secondary linker (glutaraldehyde) of the particles produced in Example 8 by incubation of the reduced IgG, in a phosphate buffered saline solution, at 37° C. for 90 minutes.

For visualization (microscopy) and quantitative determination (fluorometry) of antibody attachment, a specific anti-mouse IgG F(ab')$_2$ fragment, conjugated with Cy3 fluorescent marker, was contacted with the particles having the IgG antibody attached. The fluorescently-labeled anti-mouse IgG F(ab')$_2$ fragment, in a phosphate buffered saline solution, was incubated in the presence of the particles having the IgG attached for 30 minutes at room temperature. The formation, by affinity binding, of the complex mouse IgG/anti-mouse IgG F(ab')$_2$ fragment was examined by epi-fluorescence microscopy and quantified by fluorometry.

Comparable results were obtained for oxidized particles produced in Examples 4 and 5 and treated with the primary and secondary linkers in Example 8.

Example 13-Attachment of Enzyme Recognition Element

Acetylcholinesterase enzyme (Sigma-Aldrich Canada Ltd.) was attached through the glutaraldehyde secondary linker of the particles produced in Example 8 by incubation of the enzyme, in a phosphate buffered saline solution, with the particles at room temperature for 90 minutes.

Figure 7:
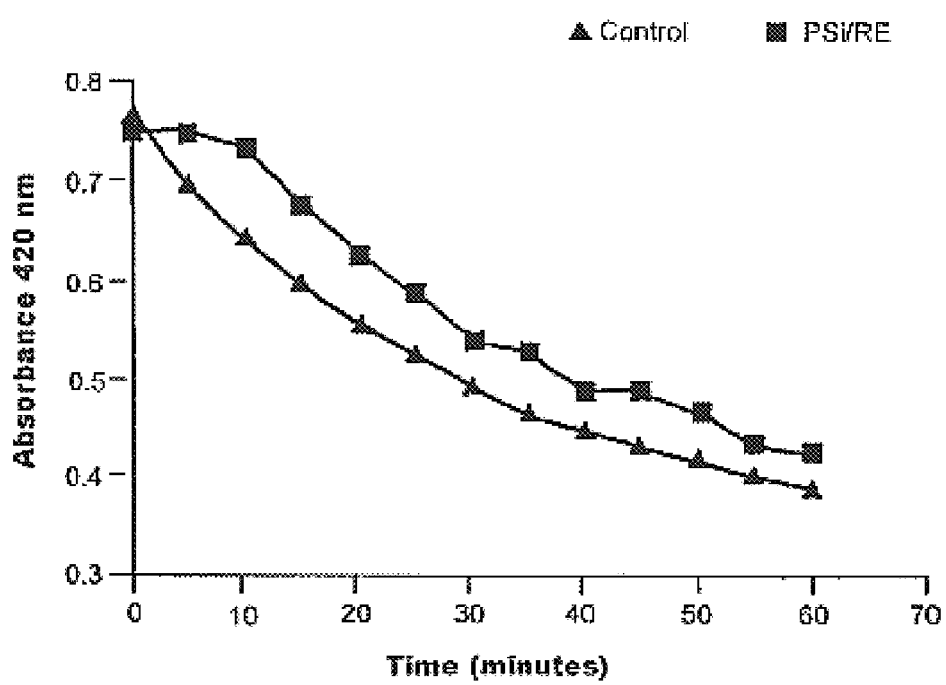
FIG. 7 graphically compares acetylcholine hydrolysis for a control enzyme versus an enzyme-modified PSi, discussed in Example 13.

FIG. 7 graphically compares acetylcholine hydrolysis for a control enzyme versus enzyme bound to the enzyme-modified PSi.

Example 14-Treatment with Protein A, Attachment of Mouse IgG Antibody

Particles produced in Example 8 were treated with Protein A by incubating the particles in a solution of Protein A in a phosphate buffered saline solution for 3 hours at 37° C. After incubation, the particles were washed with a phosphate buffered solution.

Purified mouse IgG antibody (obtained from Sigma-Aldrich Canada Ltd.) was attached to the Protein A treated particles by incubating the particles in a phosphate buffered saline solution of IgG for 90 minutes at 37° C.

For visualization (microscopy) and quantitative determination (fluorometry) of IgG attachment, a specific anti-mouse IgG F(ab')$_2$ fragment, conjugated with Cy3 fluorescent marker, was contacted with the particles having the IgG antibody attached. The fluorescently-labeled anti-mouse IgG F(ab')$_2$ fragment, in a phosphate buffered saline solution, was incubated in the presence of the particles having the IgG attached for 30 minutes at room temperature. The formation, by affinity binding, of the complex IgG/anti-mouse IgG F(ab')$_2$ fragment, used as antigen, was examined by epi-fluorescence microscopy and quantified by fluorometry.

Both epi-fluorescence microscopy and fluorometry showed good coverage and distribution of antibody recognition elements on PSi particles.

The analytes conjugated with the fluorescent markers were also used to determine whether the Protein A-treatment minimized non-specific binding of biomolecules to the Protein A-treated PSi surface, other than through the immunoglobulin attached above. Both epi-fluorescence microscopy and fluorometry showed no significant non-specific binding of biomolecules other than immunoglobulins with intact Fc domain.

Example 15-Treatment with Protein A, Attachment of Mouse Collagen IV

Particles produced in Example 8 were treated with Protein A by incubating the particles in a solution of Protein A in a phosphate buffered saline solution for 3 hours at 37° C. After incubation, the particles were washed with a phosphate buffered solution.

Purified mouse collagen IV antibody (obtained from Sigma-Aldrich Canada Ltd.) was attached to the Protein A treated particles by incubating the particles in a phosphate buffered saline solution of the mouse collagen IV antibody for 90 minutes at 37° C.

For visualization (microscopy) and quantitative determination (fluorometry) of mouse collagen IV antibody attachment, a specific anti-mouse IgG F(ab')$_2$ fragment, conjugated with fluorescein isothiocyanate (FITC, green fluorescence) fluorescent marker, obtained from Sigma-Aldrich Canada Ltd., was contacted with the particles having the antibody attached. The fluorescently-labeled anti-mouse IgG F(ab')$_2$ fragment, in a phosphate buffered saline solution, was incubated in the presence of the particles having the antibody attached for 30 minutes at room temperature. The formation, by affinity binding, of the mouse collagen IV antibody/anti-mouse IgG F(ab')$_2$ fragment complex was examined by epi-fluorescence microscopy and quantified by fluorometry.

Both epi-fluorescence microscopy and fluorometry showed good coverage and distribution of antibody recognition elements on PSi particles.

The analytes conjugated with the fluorescent markers were also used to determine whether the Protein A-treatment minimized non-specific binding of biomolecules to the Protein A-treated PSi surface, other than through the immunoglobulin attached above. Both epi-fluorescence microscopy and fluorometry showed no significant non-specific binding of biomolecules other than immunoglobulins with intact Fc domain.

Example 16-Treatment with Blocking Solution

Minimization of non-specific binding by using a blocking solution was tested on the particles produced in Examples 6, 8 and 9. The particles were treated with a glycine buffer (either 50 mM or 200 mM at either pH 8.6 or pH 10) for 30 and 60 minutes at room temperature. After incubation of the particles in glycine buffer, mouse IgG (used here as a test substance having amine reactive groups) conjugated with Cy3 fluorescent marker was incubated with the particles at 37° C. for 90 minutes. After protein incubation, the particles were washed with a phosphate buffered saline solution. Determination of the blocking effect of the glycine buffer, i.e. the ability of the buffer to inhibit binding of protein on the linkers, was done by assessment of the fluorescently-labeled IgG binding on the particles. Both epi-fluorescence microscopy and fluorometry showed a significantly reduced, >70%, binding of antibodies on the treated PSi particles. Similar results were obtained for particles produced in Examples 6, 8 and 9.

Figure 8:
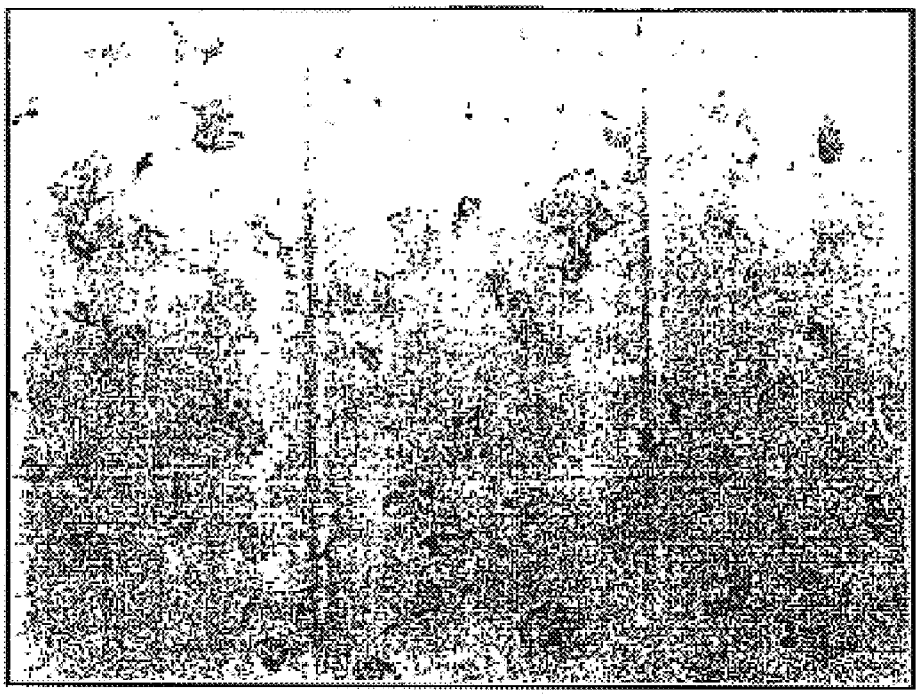
FIG. 8 is an epi-fluorescence micrograph at 200X magnification which shows binding of antibody to PSi not treated with glycine buffer, discussed in Example 16.
Figure 9:
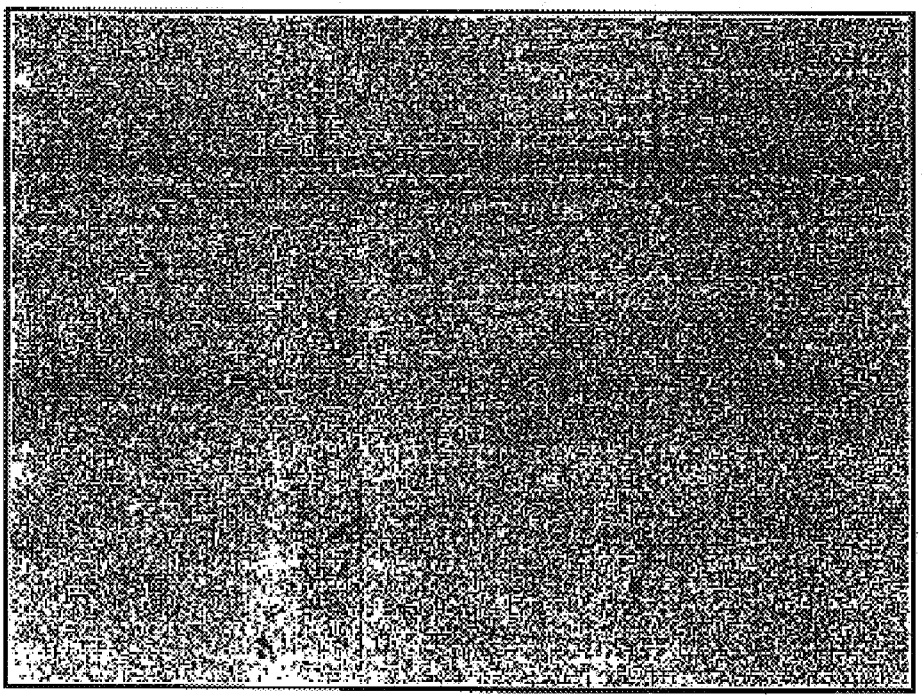
FIG. 9 is an epi-fluorescence micrograph at 200X magnification which demonstrates the reduction in binding of antibody of PSi treated with glycine buffer, discussed in Example 16.

FIG. 8 is an epi-fluorescence micrograph at 200X magnification which shows binding of antibody to PSi not treated with glycine buffer. FIG. 9 is an epi-fluorescence micrograph at 200X magnification which demonstrates the reduction in binding of antibody of PSi treated with glycine buffer.

In practice, recognition elements would be attached to the PSc particles prior to treatment with the blocking solution. The blocking solution would not interfere with binding of a target analyte to the recognition element, but would minimize binding of non-target compounds and the target analyte directly to the surface of the PSc.

In order to verify that the glycine buffer has no detrimental effect on the ability for IgG to interact with an antigen, a specific anti-mouse IgG F(ab')$_2$ fragment, conjugated with fluorescein isothiocyanate fluorescent marker was added to the IgG for a 30 minute incubation at room temperature. The binding activity of IgG, following incubation in glycine buffer, was assessed by epi-fluorescence microscopy and fluorometry. No detrimental effect of the glycine buffer on the subsequent affinity binding activity of IgG was observed.

Figure 10:
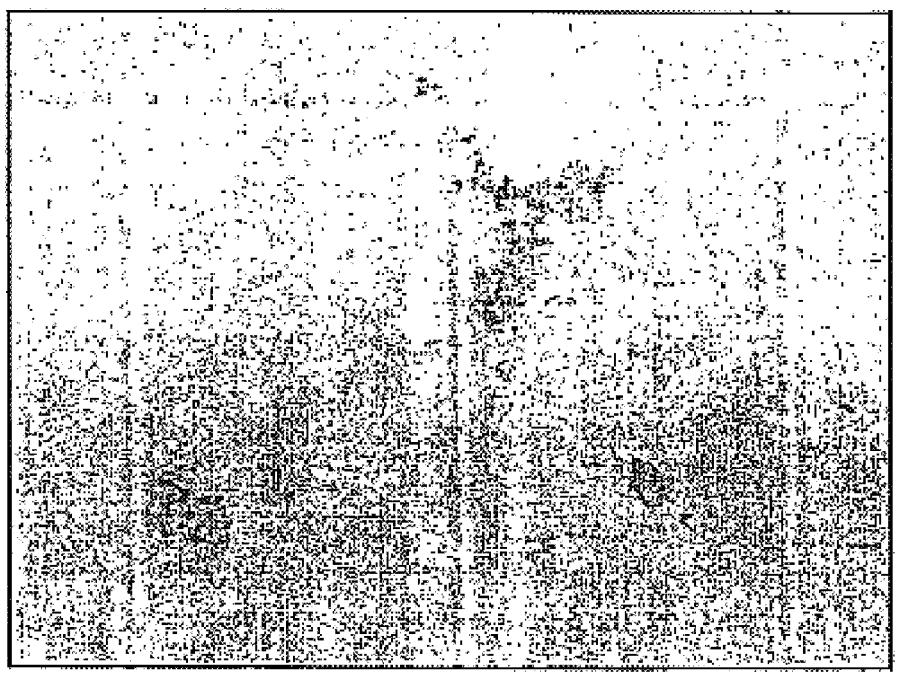
FIG. 10 is an epi-fluorescent micrograph at 200X magnification which shows binding activity of antibody in FIG. 9 is not adversely affected by glycine buffer, discussed in Example 16.

FIG. 10 is an epi-fluorescent micrograph at 200X magnification which shows binding activity of antibody in FIG. 9 is not adversely affected by glycine buffer.

Example 17-Characterization of Photoluminescence

The apparatus depicted in FIG. 1 was used to analyze photoluminescence of a number of samples produced in the above Examples. Light having a wavelength of 488 nm was directed at the sample. The spectral sensitivity of the photodiode was in the range of from about 420 nm to about 1100 nm.

Figure 11:
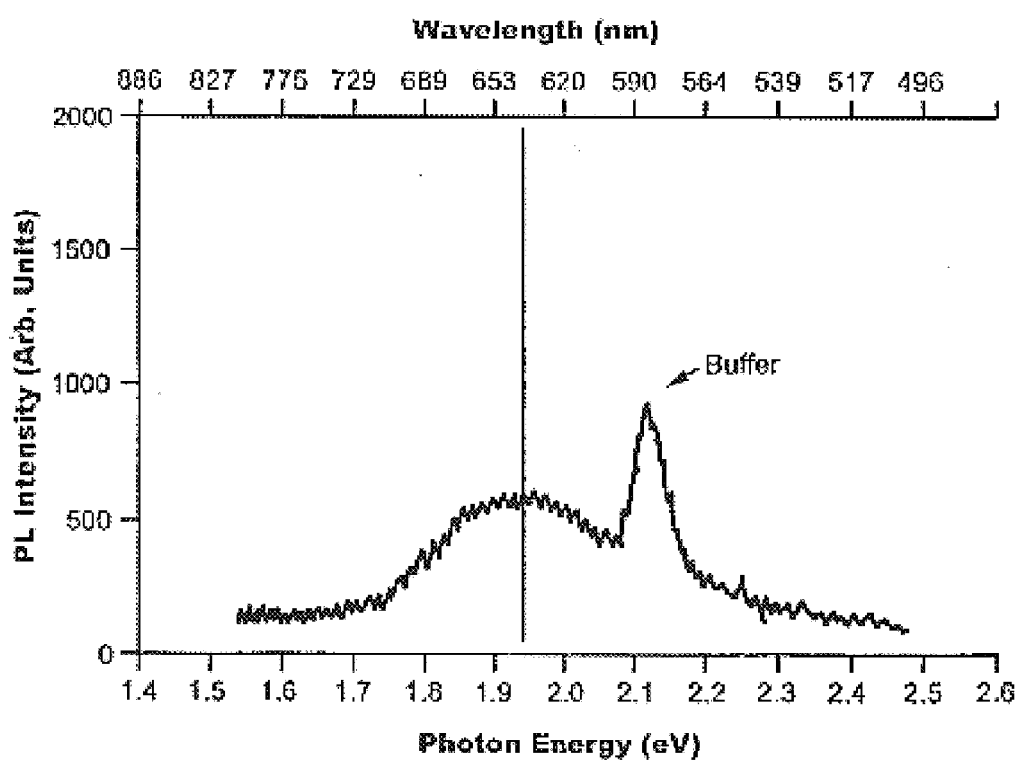
FIG. 11 is a graphical representation of photoluminescence intensity of porous silicon particles discussed in Example 17.

The photoluminescence of PSi particles produced in Example 1 was analyzed and the PL intensity is graphically represented as a function of photon energy and wavelength in FIG. 11. The PL intensity maximum was about 625 arbitrary units at about 1.94 eV.

Figure 12:
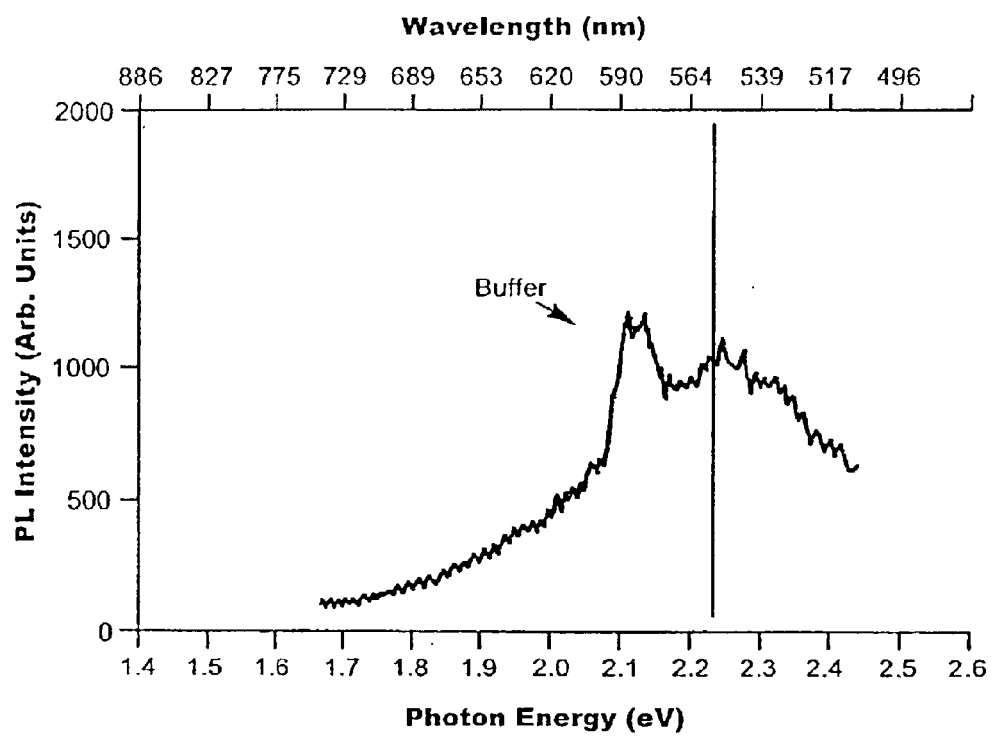
FIG. 12 is a graphical representation of photoluminescence intensity of porous silicon particles having a recognition element attached thereto discussed in Example 17.

The photoluminescence of PSi particles having an antibody recognition element attached thereto, produced in Example 8, was then analyzed. The PL intensity is graphically represented as a function of photon energy and wavelength in FIG. 12. The PL intensity maximum was about 1000 arbitrary units at about 2.24 eV.

Figure 13:
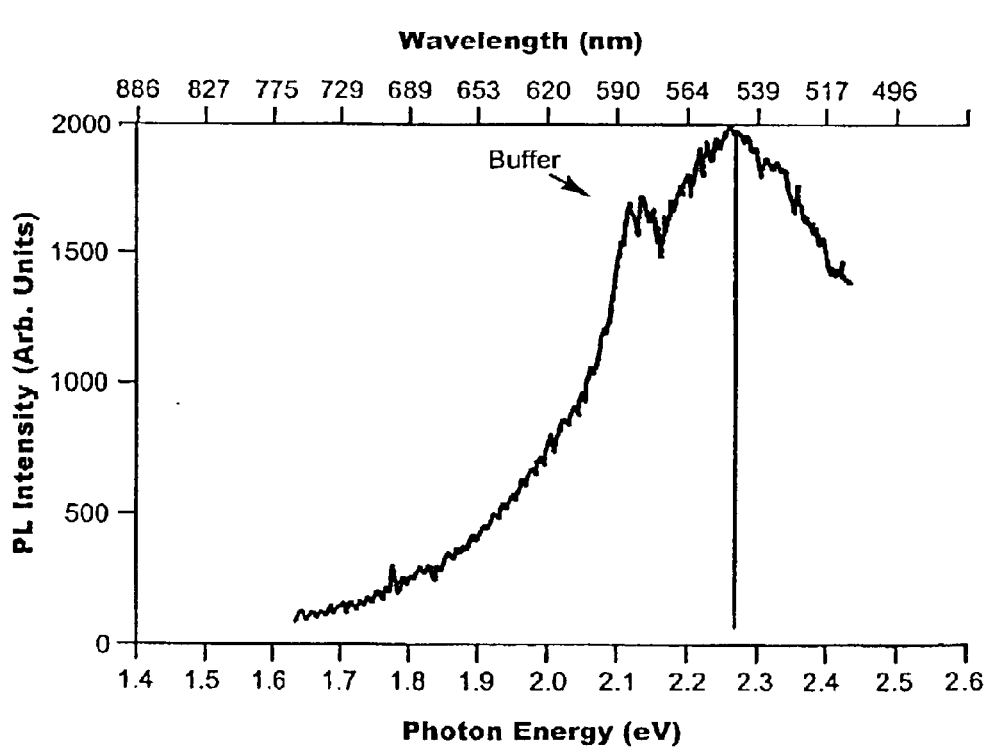
FIG. 13 is a graphical representation of photoluminescence intensity of porous silicon particles having a target analyte attached to a recognition element discussed in Example 17.

The photoluminescence of PSi particles having an antibody recognition element attached thereto, produced in Example 8, and an anti-mouse IgG target analyte attached to the recognition element was then analyzed. The PL intensity is graphically represented as a function of photon energy and wavelength in FIG. 13. The PL intensity maximum was about 1900 arbitrary units at about 2.27 eV.

The photoluminescence patterns discussed above show significant, distinct and reproducible PL pattern modulations. The expected luminescent signal, of lower energy in the orange-red region of the visible spectrum, emitted by the PSi particle of Example 1 show an increase in energy, in the yellow region of the spectrum, on attachment of a recognition element and a distinct higher energy signal in the green region of the spectrum generated by attachment of the target analyte to the recognition element. The photoluminescence emission, measured using the apparatus of FIG. 1 described above, is intense and readily distinguishable by eye, i.e. there was strong visible light emission.

Preferred embodiments of the present invention have been described. It will be understood that the foregoing is illustrative only and that other embodiments and applications can be employed without departing from the true scope of the invention described in the following claims.

We claim:

1. A method for detecting a target analyte comprising:
   (a) irradiating a complex with at least one wavelength of electromagnetic radiation in the range of from about 100 nm to about 1000 nm, wherein said complex comprises a sample suspected of containing said target analyte and a sensor composition, and
   (b) detecting a luminescent response in the range of from about 200 to about 800 nm, wherein said sensor composition comprises at least one porous semiconductor material modified with at least one recognition element,
   wherein the pore structure of said porous semiconductor material is substantially free of retaining pores,
   wherein said recognition element is capable of specifically binding to said target analyte, and
   wherein said luminescent response is produced by said porous semiconductor composition and is modified upon binding of said target analyte to said recognition element.

2. A method for detecting a target analyte comprising:
   (a) irradiating a complex with at least one wavelength of electromagnetic radiation in the range of from about 100 nm to about 1000 nm, wherein said complex comprises a sample suspected of containing said target analyte and a sensor composition, and
   (b) detecting a luminescent response in the range of from about 200 nm to about 800 nm,
   wherein said sensor composition comprises at least one porous semiconductor material modified with at least one recognition element,
   wherein said porous semiconductor material has a surface area of up to about 11 times the surface area of a corresponding non-porous semiconductor material,
   wherein said recognition element is capable of specifically binding to said target analyte, and
   wherein said luminescent response is produced by said porous semiconductor composition and is modified upon binding of said target analyte to said recognition element.

3. The method according to claim 1, wherein the surface of said semiconductor material comprises mixtures of depressions or protrusions selected from the group consisting of circular, semi-circular, ellipsoidal, semi-ellipsoidal, polygonal, square, rectangular, triangular, rhomboidal, trapezial, trapezoidal, cylindrical, conical, cubical, parallelepipedal, polyhedral, rhombohedral, ellipsoidal, helical, spherical, ovoidal, pyramidal shapes, and combinations thereof.

4. A method for detecting a target analyte comprising:
   (a) irradiating a complex with at least one wavelength of electromagnetic radiation in the range of from about 100 nm to about 1000 nm, wherein said complex comprises a sample suspected of containing said target analyte and a sensor composition, and
   (b) detecting a luminescent response in the range of from about 200 nm to about 800 nm,
   wherein said sensor composition comprises at least one semiconductor material modified with at least one recognition element,
   wherein the surface of said semiconductor material comprises substantially irregular structural features,
   wherein said recognition element is capable of specifically binding to said target analyte, and
   wherein said luminescent response is produced by said porous semiconductor composition and is modified upon binding of said target analyte to said recognition element.

5. A method for detecting a target analyte comprising:
   (a) irradiating a complex with at least one wavelength of electromagnetic radiation in the range of from about 100 nm to about 1000 nm, wherein said complex comprises a sample suspected of containing said target analyte and a sensor composition, and
   (b) detecting a luminescent response in the range of from about 200 nm to about 800 nm,
   wherein said sensor composition comprises at least one porous semiconductor material modified with at least one recognition element,
   wherein the pores of said porous semiconductor material are distributed in a substantially irregular fashion, wherein said recognition element is capable of specifically binding to said target analyte, and wherein said luminescent response is produced by said porous semiconductor composition and is modified upon binding of said target analyte to said recognition element.

6. A method for detecting a target analyte comprising:

(a) irradiating a complex with at least one wavelength of electromagnetic radiation in the range of from about 100 nm to about 1000 nm, wherein said complex comprises a sample suspected of containing said target analyte and a sensor composition, and (b) detecting a luminescent response in the range of from about 200 nm to about 800 nm, wherein said sensor composition comprises at least one porous semiconductor material modified with at least one recognition element, wherein said porous semiconductor material has a three dimensional shape that is not a film or a wafer, wherein said recognition element is capable of specifically binding to said target analyte, and wherein said luminescent response is produced by said porous semiconductor composition and is modified upon binding of said target analyte to said recognition element.

7. A method for detecting a target analyte comprising:

(a) irradiating a complex with at least one wavelength of electromagnetic radiation in the range of from about 100 nm to about 1000 nm, wherein said complex comprises a sample suspected of containing said target analyte and a sensor composition, and (b) detecting a luminescent response in the range of from about 200 nm to about 800 nm, wherein said sensor composition comprises at least one porous semiconductor material modified with at least one recognition element, wherein said porous semiconductor material has a particulate structure, wherein said recognition element is capable of specifically binding to said target analyte, and wherein said luminescent response is produced by said porous semiconductor composition and is modified upon binding of said target analyte to said recognition element.

8. A method for detecting a target analyte comprising:

(a) irradiating a complex with at least one wavelength of electromagnetic radiation in the range of from about 100 nm to about 1000 nm, wherein said complex comprises a sample suspected of containing said target analyte and a sensor composition, and (b) detecting a luminescent response in the range of from about 200 nm to about 800 nm, wherein said sensor composition comprises a core material having a coating at least one layer of a porous semiconductor material modified with at least one recognition element, wherein said porous semiconductor material has a particulate structure, wherein said recognition element is capable of specifically binding to said target analyte, and wherein said luminescent response is produced by said porous semiconductor composition and is modified upon binding of said target analyte to said recognition element.

9. The method according to any of claims 1–8, wherein said recognition element is selected from the group consisting of proteins, nucleic acids, oligonucleotides, lectins, carbohydrates, glycoproteins, lipids and combinations thereof.

10. The method according to any of claims 1–8, wherein said target analyte is selected from the group consisting of antigens, enzyme substrates, nerve agents, pesticides, insecticides, nucleic acids, receptor ligands and lectins.

11. The method according to any of claims 1–8, wherein said recognition element is covalently bonded to said semiconductor material.

12. The method according to claim 1 wherein said recognition element is bound to said semiconductor material via at least one primary linker.

13. The method according to claim 12, wherein said sensor composition further comprises a linker treatment composition.

14. The method according to claim 13, wherein said linker treatment composition is selected from the group consisting of immunoglobulin binding proteins, biotin reactive agents, blocking solutions and combinations thereof.

15. The method according to any of claims 1–8, wherein said semiconductor material is selected from the group consisting of silicon, silicon carbide, silicon dioxide, germanium, gallium, gallium arsenide, silicon gallium phosphide, cadmium, selenium, copper oxide and combinations thereof.

16. The method according to any of claims 1–8, wherein said semiconductor composition further comprises a dopant for said semiconductor material.

17. The method according to claim 16, wherein said dopant is selected from the group consisting of erbium, boron, phosphorous, copper, phosphors from the lanthanides series and combinations thereof.

18. The method according to any of claims 1–7, wherein said semiconductor material further comprises a core material as a support for said semiconductor material.

19. The method according to claim 18, wherein said core material is selected from the group consisting of glass, plastic, ceramics, zeolites, metals and combinations thereof.

20. A method for detecting an organism comprising:

(a) irradiating a complex with at least one wavelength of electromagnetic radiation in the range of from about 100 nm to about 1000 nm, wherein said complex comprises a sample suspected of containing said organism and a sensor composition, and (b) detecting a luminescent response in the range of from about 200 nm to about 800 nm, wherein said sensor composition comprises at least one porous semiconductor material modified with at least one recognition element, wherein said recognition element is capable of specifically binding to said organism, and wherein said luminescent response is produced by said porous semiconductor composition and is modified upon binding of said target analyte to said recognition element.

21. The method composition according to claim 20, wherein said recognition element is selected from the group consisting of proteins, lectins, carbohydrates, glycoproteins, and combinations thereof.

22. The method according to claim 21, wherein said recognition element is covalently bonded to said semiconductor material.

23. The method according to claim 21, wherein said recognition element is bound to said semiconductor material via at least one primary linker.

24. The method according to claim 23, wherein said semiconductor composition further comprises a linker treatment composition.

25. The method according to claim 24, wherein said linker treatment composition is selected from the group consisting of immunoglobulin Finding proteins, biotin reactive agents, blocking solutions and combinations thereof.

26. The method according to claim 20, wherein said semiconductor material is selected from the group consisting of silicon, silicon carbide, silicon dioxide, germanium, gallium, gallium arsenide, silicon gallium phosphide, cadmium, selenium, copper oxide and combinations thereof.

27. The method according to claim 20, further comprising a dopant for said semiconductor material.

28. The method according to claim 17, wherein said dopant is selected from the group consisting of erbium, boron, phosphorous, copper, phosphors from the lanthanides series and combinations thereof.

29. The method according to claim 20, wherein said semiconductor material further comprises a core material as a support for said semiconductor material.

30. The method according to claim 29, wherein said core material is selected from the group consisting of glass, plastic, ceramics, zeolites, metals and combinations thereof.

31. The method according to claim 6, wherein said at least one porous semiconductor material comprises silicon.

32. The composition according to claim 6, wherein said at least one porous semiconductor material has a diameter in the range of at least about 100 nm.

33. The method according to any of claims 1–8 or 20, wherein the intensity of said luminescent response is modified upon binding of said target analyte to said recognition element.

34. The method according to any of claims 1–8, or 20, wherein the wavelength of said luminescent response is modified upon binding of said target analyte to said recognition element.

* * * * *